(12) United States Patent
Birr et al.

(10) Patent No.: US 7,851,435 B2
(45) Date of Patent: Dec. 14, 2010

(54) BONE MORPHOGENETIC PROTEIN 3 AND OSTEOGENIC DEVICES AND PHARMACEUTICAL PRODUCTS CONTAINING THEREOF

(75) Inventors: Elli Birr, Kempele (FI); Mari Ulmanen, Tampere (FI); Oili Hietala, Oulu (FI); Marja Juustila, Liminka (FI); Heli Korkala, Oulu (FI); Pekka Jalovaara, Oulu (FI)

(73) Assignee: BBS-Bioactive Bone Substitutes Oy, Oulu (FI)

( * ) Notice: Subject to any disclaimer, the term of this patent is extended or adjusted under 35 U.S.C. 154(b) by 268 days.

(21) Appl. No.: 11/921,104

(22) PCT Filed: May 26, 2006

(86) PCT No.: PCT/FI2006/050212

§ 371 (c)(1),
(2), (4) Date: Jan. 12, 2008

(87) PCT Pub. No.: WO2006/125866

PCT Pub. Date: Nov. 30, 2006

(65) Prior Publication Data

US 2010/0041595 A1   Feb. 18, 2010

(30) Foreign Application Priority Data

May 27, 2005 (FI) ................................. 20055256
May 27, 2005 (FI) ................................. 20055257

(51) Int. Cl.
*A61K 38/16* (2006.01)
*A61K 38/17* (2006.01)
*A61K 38/18* (2006.01)
*C12N 15/11* (2006.01)
*C12N 15/12* (2006.01)
*C12N 15/63* (2006.01)
*C12N 1/21* (2006.01)
*C12N 1/19* (2006.01)
*C12N 5/10* (2006.01)

(52) U.S. Cl. ........................... 514/2; 530/351; 536/23.1; 536/23.5; 435/320.1; 435/252.3; 435/254.11; 435/325

(58) Field of Classification Search ....................... None
See application file for complete search history.

(56) References Cited

U.S. PATENT DOCUMENTS 6,204,047 B1   3/2001   Lee et al.

FOREIGN PATENT DOCUMENTS

| WO | 94/01557 A1 | 1/1994 |
| WO | WO 2004/061125 | 7/2004 |

OTHER PUBLICATIONS

Uniprot database entry Q08DX6, bovine bone morphogenic protein-3b, May 2007.*
Wells, 1990, Biochemistry 29:8509-8517.*
Ngo et al., 1994, The Protein Folding Problem and Tertiary Structure Prediction, Merz et al., eds., Birkhauser, Boston, pp. 492-495.*
European search report dated Feb. 2, 2009 in corresponding EP 06725969.
Database EMBL [Online], Mar. 11, 2005, "1254007 MARC 7BOV Bos taurus cDNA 5;, mRNA sequence", XP002513027.
Kapanen A et al., "Bone morphogenetic protein 3b expressing reindeer antler", Journal of Biomedical Materials Research Jan. 2002, vol. 59, No. 1, Jan. 2002, pp. 78-83, XP002513026.
Takao M et al., "Identification of rat bone morphogenetic protein -3b (BMP-3b), a new member of BMP-3", Biochemical and Biophysical Research Communications, Academic Press Inc., vol. 219, No. 2, Jan. 1, 1996, pp. 656-662, XP002351080.
European Search Report in Corresponding Application No. 06725969.7 Dated Apr. 20, 2010.

* cited by examiner

*Primary Examiner*—Elizabeth C. Kemmerer
(74) *Attorney, Agent, or Firm*—Young & Thompson

(57) ABSTRACT

The present invention relates to reindeer bone formation inducing protein called bone morphogenetic protein 3c (BMP-3c), nucleotide molecules encoding the protein and host cells expressing the protein. The present invention relates also to the use of said BMP-3c for treating disorders related to bone and cartilage formation. Osteogenic devices and pharmaceutical compositions containing the protein are also disclosed.

20 Claims, 8 Drawing Sheets

| 1 | atg | gat | ccg | agg | aag | aag | ggc | cag | gat | gtt | ttc | atg | gcc | tcc | tca | 39 |
|---|---|---|---|---|---|---|---|---|---|---|---|---|---|---|---|---|
| | M | D | P | R | K | K | G | Q | D | V | F | M | A | S | S | |
| | | | | | 5 | | | | | 10 | | | | | 15 | |

| 40 | cag | gtg | ctg | gac | ttt | gac | gag | aag | acg | atg | cag | aaa | gcc | cgg | aag | 78 |
|---|---|---|---|---|---|---|---|---|---|---|---|---|---|---|---|---|
| | Q | V | L | D | F | D | E | K | T | M | Q | K | A | R | K | |
| | | | | | 20 | | | | | 25 | | | | | 30 | |

| 79 | aag | caa | tgg | gat | gag | cca | cgg | gtc | tgt | tcc | cgg | agg | tat | ctg | aag | 117 |
|---|---|---|---|---|---|---|---|---|---|---|---|---|---|---|---|---|
| | K | Q | W | D | E | P | R | V | C | S | R | R | Y | L | K | |
| | | | | | 35 | | | | | 40 | | | | | 45 | |

| 118 | gtg | gac | ttc | gcg | gac | ata | ggg | tgg | aat | gaa | tgg | atc | atc | tca | ccc | 156 |
|---|---|---|---|---|---|---|---|---|---|---|---|---|---|---|---|---|
| | V | D | F | A | D | I | G | W | N | E | W | I | I | S | P | |
| | | | | | 50 | | | | | 55 | | | | | 60 | |

| 157 | aag | tct | ttc | gac | gcc | tac | tac | tgc | tca | gga | gcc | tgc | gag | ttc | ccc | 195 |
|---|---|---|---|---|---|---|---|---|---|---|---|---|---|---|---|---|
| | K | S | F | D | A | Y | Y | C | S | G | A | C | E | F | P | |
| | | | | | 65 | | | | | 70 | | | | | 75 | |

| 196 | atg | ccc | aag | atg | gtc | cgc | cca | tcc | aac | cac | gcc | acc | atc | cag | agc | 234 |
|---|---|---|---|---|---|---|---|---|---|---|---|---|---|---|---|---|
| | M | P | K | M | V | R | P | S | N | H | A | T | I | Q | S | |
| | | | | | 80 | | | | | 85 | | | | | 90 | |

| 235 | atc | gtc | agg | gcc | gtg | ggc | atc | gtc | cca | ggc | atc | cca | gag | ccg | tgc | 273 |
|---|---|---|---|---|---|---|---|---|---|---|---|---|---|---|---|---|
| | I | V | R | A | V | G | I | V | P | G | I | P | E | P | C | |
| | | | | | 95 | | | | | 100 | | | | | 105 | |

| 274 | tgt | gtt | ccc | gac | aag | atg | agc | tct | ctt | ggg | gtc | ctt | ttc | ctg | gat | 312 |
|---|---|---|---|---|---|---|---|---|---|---|---|---|---|---|---|---|
| | C | V | P | D | K | M | S | S | L | G | V | L | F | L | D | |
| | | | | | 110 | | | | | 115 | | | | | 120 | |

| 313 | gag | aac | cgg | aac | gtg | gta | ctg | aag | gtg | tac | ccc | aac | atg | tct | gtg | 351 |
|---|---|---|---|---|---|---|---|---|---|---|---|---|---|---|---|---|
| | E | N | R | N | V | V | L | K | V | Y | P | N | M | S | V | |
| | | | | | 125 | | | | | 130 | | | | | 135 | |

| 352 | gag | acc | tgt | gcc | tgc | caa | aag | ctt | ggg | ccc | gaa | caa | aaa | ctc | atc | 390 |
|---|---|---|---|---|---|---|---|---|---|---|---|---|---|---|---|---|
| | E | T | C | A | C | Q | K | L | G | P | E | Q | K | L | I | |
| | | | | | 140 | | | | | 145 | | | | | 150 | |

| 391 | tca | gaa | gag | gat | ctg | aat | agc | gcc | gtg | gac | cat | cat | cat | cat | cat | 429 |
|---|---|---|---|---|---|---|---|---|---|---|---|---|---|---|---|---|
| | S | E | E | D | L | N | S | A | V | D | H | H | H | H | H | |
| | | | | | 155 | | | | | 160 | | | | | 165 | |

| 430 | cat | tga | | | | | | | | | | | | | | 436 |
|---|---|---|---|---|---|---|---|---|---|---|---|---|---|---|---|---|
| | H | - | | | | | | | | | | | | | | |

Fig. 4

| | | | | | | | | | | | | | | | |
|---|---|---|---|---|---|---|---|---|---|---|---|---|---|---|---|
| 1 | atg M | aaa K | tac Y | ctg L 5 | ctg L | ccg P | acc T | gct A | gct A | gct A 10 | ggt G | ctg L | ctg L | ctc L | ctc L 15 | 45 |
| 46 | gct A | gcc A | cag Q | ccg P | gcg A 20 | atg M | gcc A | atg M | gat D | atc I 25 | gga G | att I | aat N | tcg S | gat D 30 | 90 |
| 91 | ccg P | agg R | aag K | aag K | ggc G 35 | cag Q | gat D | gtt V | ttc F | atg M 40 | gcc A | tcc S | tca S | cag Q | gtg V 45 | 135 |
| 136 | ctg L | gac D | ttt F | gac D | gag E 50 | aag K | acg T | atg M | cag Q | aaa K 55 | gcc A | cgg R | aag K | aag K | caa Q 60 | 180 |
| 181 | tgg W | gat D | gag E | cca P | cgg R 65 | gtc V | tgt C | tcc S | cgg R | agg R 70 | tat Y | ctg L | aag K | gtg V | gac D 75 | 225 |
| 226 | ttc F | gcg A | gac D | ata I | ggg G 80 | tgg W | aat N | gaa E | tgg W | atc I 85 | atc I | tca S | ccc P | aag K | tct S 90 | 270 |
| 271 | ttc F | gac D | gcc A | tac Y | tac Y 95 | tgc C | tca S | gga G | gcc A | tgc C 100 | gag E | ttc F | ccc P | atg M | ccc P 105 | 315 |
| 316 | aag K | atg M | gtc V | cgc R | cca P 110 | tcc S | aac N | cac H | gcc A | acc T 115 | atc I | cag Q | agc S | atc I | gtc V 120 | 360 |
| 361 | agg R | gcc A | gtg V | ggc G | atc I 125 | gtc V | cca P | ggc G | atc I | cca P 130 | gag E | ccg P | tgc C | tgt C | gtt V 135 | 405 |
| 406 | ccc P | gac D | aag K | atg M | agc S 140 | tct S | ctt L | ggg G | gtc V | ctt L 145 | ttc F | ctg L | gat D | gag E | aac N 150 | 450 |
| 451 | cgg R | aac N | gtg V | gta V | ctg L 155 | aag K | gtg V | tac Y | ccc P | aac N 160 | atg M | tct S | gtg V | gag E | acc T 165 | 495 |
| 496 | tgt C | gcc A | tgc C | caa Q | aag K 170 | ctt L | gcg A | gcc A | gca A | ctc L 175 | gag E | cac H | cac H | cac H | cac H 180 | 540 |
| 541 | cac H | cac H | tga stop | | | | | | | | | | | | | 549 |

Fig. 5

| | | | | | | | | | | | | | | | |
|---|---|---|---|---|---|---|---|---|---|---|---|---|---|---|---|
| 1 | cgc R | aag K | gac D | cgc R | agg R | aag K | aag K | ggc G | cag Q | gat D | gtt V | ttc F | atg M | gcc A | tcc S | 45 |
| | | | | | | | | 5 | | | 10 | | | | 15 |
| 46 | tca S | cag Q | gtg V | ctg L | gac D | ttt F | gac D | gag E | aag K | acg T | atg M | cag Q | aaa K | gcc A | cgg R | 90 |
| | | | | | | | | 20 | | | 25 | | | | 30 |
| 91 | aag K | aag K | caa Q | tgg W | gat D | gag E | cca P | cgg R | gtc V | tgt C | tcc S | cgg R | agg R | tat Y | ctg L | 135 |
| | | | | | | | | 35 | | | 40 | | | | 45 |
| 136 | aag K | gtg V | gac D | ttc F | gcg A | gac D | ata I | ggg G | tgg W | aat N | gaa E | tgg W | atc I | atc I | tca S | 180 |
| | | | | | | | | 50 | | | 55 | | | | 60 |
| 181 | ccc P | aag K | tct S | ttc F | gac D | gcc A | tac Y | tac Y | tgc C | tca S | gga G | gcc A | tgc C | gag E | ttc F | 225 |
| | | | | | | | | 65 | | | 70 | | | | 75 |
| 226 | ccc P | atg M | ccc P | aag K | atg M | gtc V | cgc R | cca P | tcc S | aac N | cac H | gcc A | acc T | atc I | cag Q | 270 |
| | | | | | | | | 80 | | | 85 | | | | 90 |
| 271 | agc S | atc I | gtc V | agg R | gcc A | gtg V | ggc G | atc I | gtc V | cca P | ggc G | atc I | cca P | gag E | ccg P | 315 |
| | | | | | | | | 95 | | | 100 | | | | 105 |
| 316 | tgc C | tgt C | gtt V | ccc P | gac D | aag K | atg M | agc S | tct S | ctt L | ggg G | gtc V | ctt L | ttc F | ctg L | 360 |
| | | | | | | | | 110 | | | 115 | | | | 120 |
| 361 | gat D | gag E | aac N | cgg R | aac N | gtg V | gta V | ctg L | aag K | gtg V | tac Y | ccc P | aac N | atg M | tct S | 405 |
| | | | | | | | | 125 | | | 130 | | | | 135 |
| 406 | gtg V | gag E | acc T | tgt C | gcc A | tgc C | caa Q | | | | | | | | | 450 |
| | | | | | 140 | | | | | | | | | | |

Fig. 6 ary foundgrounds of the invention and some relevant prior art… 

BONE MORPHOGENETIC PROTEIN 3 AND OSTEOGENIC DEVICES AND PHARMACEUTICAL PRODUCTS CONTAINING THEREOF

FIELD OF THE INVENTION

The present invention relates to bone formation inducing proteins called bone morphogenetic proteins (BMP), especially BMP-3c, nucleic acid molecules encoding said proteins, vectors containing said nucleic acid molecules and host cells expressing said proteins. The present invention relates also to the use of said bone morphogenetic proteins for treating disorders, such as disorders related to bone and cartilage formation. The present invention further relates to osteogenic devices and pharmaceutical compositions containing said proteins.

BACKGROUND OF THE INVENTION

The phenomenon of osteoinduction was recognized by Lancroix in 1945 when he demonstrated that acid alcohol bone extracts induced heterotopic bone formation in ectopic sites. Twenty years later Urist and his co-workers decalcified bone matrix and observed new cartilage and bone formation when implanted intramuscularly. These discoveries led to isolation and purification of bone inducing agent named BMPs from bone matrix of different species and years later to cloning and characterization of several cDNAs encoding these novel proteins. The biological activity of BMPs has been determined by bioassay in rat or mouse muscle bounces or by ALP measurements in mammalian cell cultures.

Previous studies since 1965 have shown that BMPs are part of the TGF-β superfamily and like all the family members they have multiple effects on cell migration, growth and differentiation especially in bone formation and tissue repair but also in embryogenesis or cancer. They are low molecular weight hydrophobic glycoproteins which are soluble to chaotrophic agents such as urea and guanidinium hydrochloride but are resistant to several proteases, for example collagenases.

BMPs are produced as large precursor molecules which are processed proteolytically to mature peptides after the translation. Like all the members of TGF-β superfamily, BMPs have the pattern of seven cysteine residues in their C-terminal mature region. Between these cysteines there are three disulfide bonds within mature BMP monomers and one disulfide bond which combines two monomers into a biologically active BMP dimer.

BMPs act through specific transmembrane receptors located on cell surface of the target cells. The BMP receptors are serin-threonin kinases which resemble TGF-β receptors and are divided into two subgroups: type I and type II receptors. BMPs can bind strongly only to the heterotetrameric complex of these receptors. This complex formation is essential to the BMP signal transduction. Inside the target cell, BMP signals are transmitted to the nucleus via specific signal molecules called Smads, which are also responsible for suppression of BMP signals.

Until now, 16 different BMPs have been characterized and seven of them (BMPs 2-7 and 9) have shown to be able to induce bone formation when implanted in ectopic sites. According to the amino acid sequence of the mature part these BMPs are divided into two subgroups. BMPs 2 and 4 are 86% identical and BMPs 5, 6 and 7 are 78% identical. Between these two groups the identity is only about 56%. The amino acid sequence of BMP-3 is about 45% alike with BMPs 2 and 4 and BMP-9 is 50-55% identical with BMPs 2, 4, 5, 6 and 7. Due to high homology and small variety in size, BMPs are quite difficult, very time consuming and expensive to separate, purify and identify from each other at protein level. This is the reason why most of the BMPs are nowadays being produced using molecular biological tools. Different kinds of recombinant protein techniques have been tested and both eukaryotic and prokaryotic systems have been utilized.

Majority of research has focused on human recombinant BMPs, but with regard to effective bone induction antlers of Cervidae family form an interesting research area. Antlers are bony cranial organs typical to the Cervidae family and they differ from Bovidae horns in their growing pattern. Antlers grow from the tip and males cast them away once per year. It has been suggested that antlers are the fastest growing structures through the mammalian species and they are known to be the only structures that regenerate completely every year. Antlers are formed by modified endochondral ossification meaning that the process is performed through the highly vascularized cartilage model which is calcified and finally transformed into bone. Antlers form an interesting model of adult regenerating mineralized tissue and bone remodeling has been shown to continue until the time of antler casting. Although the ultimate reason for the amazing speed of antler growth has not yet been resolved, antlers have been shown to contain several BMPs. Deer antler has been proven to express BMP-2 and BMP-4 (Feng et al. 1997 Biochim Biophys Acta 1350:47-52; Feng et al. 1995 Biochim Biophys Acta 1263: 163-168). In addition reindeer antlers express BMP-3b (Kapanen et al. 2002 J Biomed Mat Res 59:78-83). Yet, it is also possible that there is one or more totally uncovered factor(s) which are responsible for antler growth speed.

Due to their osteoinductive capacity, both BMPs extracted from demineralized bone matrix and BMPs produced by recombinant technique, are very interesting and highly potential alternatives to bone grafting. Different BMPs have been used in many experimental and clinical studies.

BMP-3 and 3b are important regulator molecules in bone induction and osteogenesis. BMP-3 has been shown to be a major component of osteogenin, which has osteogenic activity, but still there is some contradictory information of biological activity of recombinant human BMP-3. According to some studies it posses osteogenic activity but some studies claim just the opposite and it has been shown to play an inhibitory role in the bone formation process being also a negative regulator of bone density. For example WO 02/43759 discloses methods and compositions for treatment of defects and disease involving osteoporosis or osteopenic conditions. Said methods comprise applying to the site of osteoporotic or osteopenic conditions a composition comprising a BMP-3 inhibitor or antagonist.

Until now, BMP-3b has been the only BMP characterized in reindeer antler tissue (Kapanen et al. 2002).

U.S. Pat. No. 6,245,889 discloses purified human BMP-2 and BMP-4 proteins and processes for producing them. Also a pharmaceutical composition comprising said BMP-4 is disclosed. As generally known in the art, these proteins and compositions may be used in the treatment of bone and cartilage defects and in wound healing and related tissue repair. Further, said pharmaceutical composition may include a matrix capable of delivering said BMP proteins to the site of bone and/or cartilage damage, providing a structure for the developing bone and cartilage and optimally capable of being resorbed into the body. Such matrices may be formed of materials presently in use for other implanted medical applications.

U.S. Pat. No. 5,399,677 discloses DNA molecules encoding mutant forms of bone morphogenetic proteins. The mutant forms of BMP can be produced bacterially and refolded to produce biologically active homodimers or heterodimers of BMP. A method of making such mutant BMP is also disclosed. Said mutant forms are useful since they are correctly folded when produced in bacterial hosts.

WO 98/51354 discloses osteogenic devices and methods of use thereof for repair of bone and cartilage defects. The method for producing new bone growth at bone defect site in a mammal comprises the step of implanting in a defect site a calcium phosphate matrix comprising at least one osteogenic protein. Said osteogenic proteins include several morphogens, such as bone morphogenetic proteins.

EP 1131087 discloses further use for morphogenetic proteins, such as BMP proteins. It is shown that exposing cancer cells to morphogens inhibits cancer cell growth and causes such cells to differentiate away from the cancerous phenotype. The use of morphogen can influence cancer cell fate and, in turn, alleviate the symptoms of cancer.

Although some applications of known BMP proteins as bone and cartilage forming inducers or for alleviating the symptoms of cancer are already known, there is still need for better methods for isolating such proteins and for better morphogenetic proteins, for example ones which possess more efficient bone forming properties or are more soluble. Such proteins would be useful for better therapeutic methods and applications. Also methods for producing such proteins would be useful.

SUMMARY OF THE INVENTION

Surprisingly in the present invention a new BMP-3 type protein, herein called BMP-3c protein, was discovered from reindeer. Despite having high sequence homology with already known BMP-3 proteins, BMP-3c has very advantageous properties related to bone and cartilage forming. Said properties are substantially better than the properties of the known corresponding BMP proteins. Said bone morphogenetic proteins of the present invention and homologues thereof are useful for inducing bone and cartilage formation in several kinds of applications, such as therapeutic applications.

The reindeer BMP-3c protein of the present invention is 95% homologous to already known reindeer BMP-3b protein and 93% homologous to known human BMP-3b. As a BMP-3b counterpart of reindeer was already known, the new protein of the invention was named BMP-3c.

One aspect of the present invention relates to an isolated bone morphogenetic protein 3 (BMP-3) containing the essential amino acids of amino acid sequence of SEQ ID NO: 1.

Another aspect of the present invention relates to a heparin binding site combined with said bone morphogenetic protein. The heparin binding site improves the expression of the recombinant BMP protein and also improves the biological activity thereof.

Another aspect of the present invention relates to an isolated DNA molecule encoding said bone morphogenetic protein.

Still another aspect of the present invention relates to a nucleic acid vector containing said isolated DNA molecule.

Still another aspect of the present invention relates to a recombinant host cell containing said DNA molecule or the nucleic acid vector mentioned above.

Still another aspect of the present invention relates to bone morphogenetic protein which is produced by culturing said recombinant host cell to express said bone morphogenetic protein and by recovering said bone morphogenetic protein from said host cell.

Still another aspect of the present invention relates to a recombinant host cell expressing said bone morphogenetic protein.

Still another aspect of the present invention relates to a pharmaceutical composition containing said bone morphogenetic protein.

Still another aspect of the present invention relates to said isolated bone morphogenetic protein for use as medicament.

Still another aspect of the present invention relates to the use of said isolated bone morphogenetic protein for manufacturing medicament for disorders related to bone or cartilage defects wherein regeneration, repair or growth thereof is desired, or other diseases, such as cancer.

Still another aspect of the present invention relates to an osteogenic device for treating said disorders said device containing said isolated bone morphogenetic protein.

Still another aspect of the present invention relates to a method for inducing the formation of cartilage and/or bone by treating said cartilage and/or bone with said isolated bone morphogenetic protein.

Still another aspect of the present invention relates to a method for treating said disorders related to bone or cartilage defects wherein regeneration, repair or growth thereof is desired, or other diseases, such as cancer, by administering said isolated bone morphogenetic protein to a patient suffering from said disorders.

Still another aspect of the present invention relates to a method for improving the expression of a recombinant BMP protein in a bacterial host by adding a heparin binding site to the amino terminus of said protein to be expressed.

Still another aspect of the present invention relates to a method for improving or enhancing the biological activity of a recombinant BMP protein by adding a heparin binding site to the amino terminus of said protein.

Still another aspect of the present invention relates to a method for expressing a BMP protein in a bacterial host, such as *E. coli*, by adding a heparin binding site to the amino terminus of said protein wherein the protein shows lowered immunogenicity when compared to a BMP expressed in for example yeast host.

BRIEF DESCRIPTION OF THE DRAWINGS

FIG. 4 Shows amino acid (SEQ ID NO: 31) and nucleotide sequences (SEQ ID NO: 30) of reindeer BMP-3c mature part expressed from pTrcrd3c. Mature part of reindeer BMP-3c is boxed and cysteine residues typical for TGF-β superfamily are marked by bold letters.

FIG. 5 Shows amino acid (SEQ ID NO: 33) and nucleotide sequences (SEQ ID NO: 32) of reindeer BMP-3c mature part expressed from pETrd3c. Mature part of reindeer BMP-3c is boxed and cysteine residues typical for TGF-β superfamily are marked by bold letters.

FIG. 6 Shows partial amino acid (SEQ ID NO: 35) and nucleotide sequences (SEQ ID NO: 34) of reindeer BMP-3c. Mature part is boxed and cysteine residues typical for TGF-β superfamily members are marked by bold letters.

DETAILED DESCRIPTION OF THE INVENTION

Figure 1:
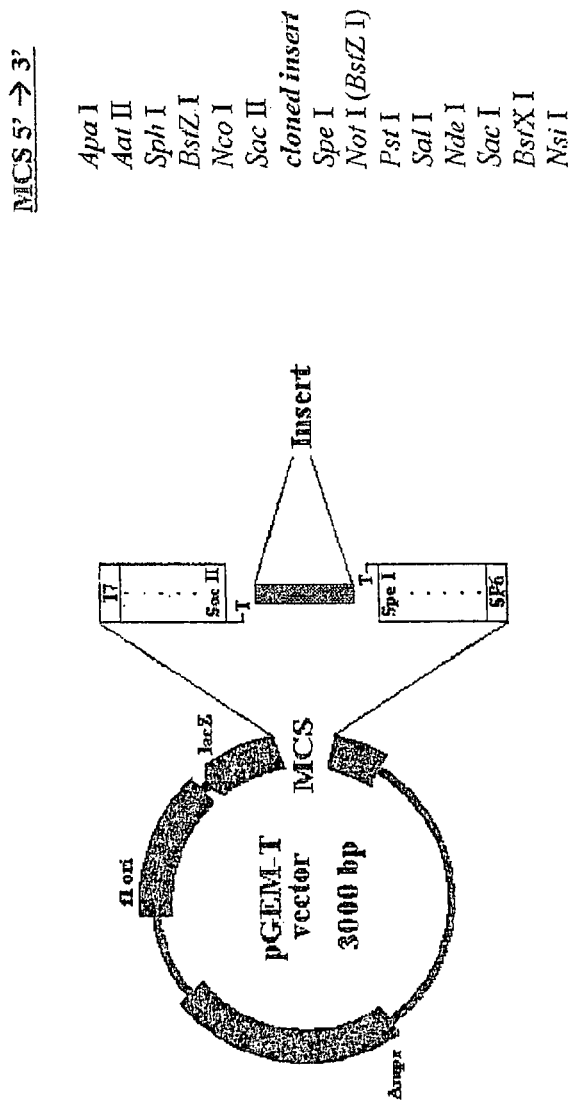
FIG. 1 shows plasmids containing rdBMP-3c inserts in PCR vector pGEM-T® (Promega).

Among mammalian species the homology of previously known BMP-3 mature parts is high. Cloning and characterization of reindeer BMP-3c mature part revealed that at the amino acid level it has the highest homology with reindeer BMP-3b (95%) and human BMP-3b (93%).

Nucleotide and amino acid homologies of BMP-3b and BMP-3 proteins between mammalian species are presented in table 1 and table 2, respectively. BMP-3b has previously been characterized from human, mouse and rat. The homology comparison at nucleotide level ranges between 87-92% and at amino acid level between 94-97%. In addition to earlier mentioned organisms BMP-3b has also been cloned from reindeer. The amino acid homology of BMP-3b from different mammalian origin ranges from 94-97% and nucleotide homology from 87-92%. The nucleotide sequence of reindeer BMP-3c and the corresponding amino acid sequence of partial cDNA of reindeer BMP-3c are shown in FIG. 6. Generally BMP-3s have homology also with other types of BMPs.

TABLE 1

Homology of BMP-3b mature parts of different mammalian origin at nucleotide and amino acid level presented as percentages (%) (nt = nucleotides, aa = amino acids).

| Organism | Human | | Mouse | | Rat | | Reindeer | | rdBMP-3c | |
| --- | --- | --- | --- | --- | --- | --- | --- | --- | --- | --- |
|  | aa | nt | aa | nt | aa | nt | aa | nt | aa | nt |
| Human | 100 | 100 | 92 | 88 | 92 | 87 | 89 | 88 | 93 | 89 |
| Mouse | 92 | 88 | 100 | 100 | 97 | 96 | 87 | 86 | 91 | 87 |
| Rat | 92 | 87 | 97 | 96 | 100 | 100 | 87 | 85 | 91 | 86 |
| Reindeer | 89 | 88 | 87 | 86 | 87 | 85 | 100 | 100 | 95 | 96 |
| rdBMP-3c | 93 | 89 | 91 | 87 | 91 | 86 | 95 | 96 | 100 | 100 |

TABLE 2

Homology of BMP-3 mature parts of different mammalian origin at nucleotide and amino acid level presented as percentages (%) (nt = nucleotides, aa = amino acids).

| Organism | Human | | Mouse | | Rat | | rdBMP-3c | |
| --- | --- | --- | --- | --- | --- | --- | --- | --- |
|  | aa | nt | aa | nt | aa | nt | aa | nt |
| Human | 100 | 100 | 94 | 88 | 97 | 87 | 81 | 69 |
| Mouse | 94 | 88 | 100 | 100 | 97 | 92 | 73 | 71 |
| Rat | 97 | 87 | 97 | 92 | 100 | 100 | 80 | 71 |
| rdBMP-3c | 81 | 69 | 73 | 71 | 80 | 71 | 100 | 100 |

The following alignment shows the amino acid sequences of human and reindeer mature BMP-3b proteins and the reindeer BMP-3c of the present invention (made with ClustalX 1.8 program (Thompson, J. D., Higgins, D. G. and Gibson, T. J. (1994) Nucleic Acids Research, 22: 4673-4680), rdBMP-3c=reindeer BMP-3c, rdBMP-3b=reindeer BMP-3b, hBMP-3b= human BMP-3b, the asterisks show the identical amino acids).

```
rdBMP-3c RKKGQDVFMASSQVLDFDEKTM-                                    (SEQ ID NO: 1)
         QKARKKQWDEPRVCSRRYLKVDFADIGWNEWIISPKSF rdBMP-3b RKKGQDVFMASSQVLDFDEKTMQKA-KKQVGEPRVCSRRYLKVDFADIGWNEWI-     (SEQ ID NO: 2)
         ISPKSF hBMP-3b  RKKGQEVFMAASQVLDFDEKTMQKAR-                                 (SEQ ID NO: 3)
         RKQWDEPRVCSRRYLKVDFADIGWNEWIISPKSF rdBMP-3c DAYYCSGACEFPMPKMVRPSNHATIQ-
         SIVRAVGIVPGIPEPCCVPDKMSSLGVLFLDENR rdBMP-3b DAYYCSGACEFPMPRWVRPSNHATIQ-
         SIVRAVGIVPGIPEPCCAPDKMSSLGVLFLDENR hBMP-3b  DAYYCAGACEFPMPKIVRPSNHATIQ-
         SIVRAVGIIPGIPEPCCVPDKMNSLGVLFLDENR rdBMP-3c NVVLKVYPNMSVETCACQ rdBMP-3b NVVLKVYPNMSVETCACQ hBMP-3b  NVVLKVYPNMSVDTCACR
```

The "BMP-3 protein of the invention" or "bone morphogenetic protein of the invention" refer to a protein having bone morphogenetic (or morphogenic as both words are used interchangeably) activity, such as BMP-3c isolated from reindeer as described herein (SEQ ID NO: 1 of the attached sequence listing or rdBMP-3c in the alignment above), and includes homologues, analogs, derivatives and fragments thereof. Such homologues or derivatives include functional derivatives of said protein, such as proteins derived from the original reindeer BMP-3c protein or any BMP from any species. The derivatives may differ in length and they may contain amino acid insertions, deletions and substitutions, as a person skilled in the art well knows. Characteristic for the BMP of the present invention, e.g. as disclosed in the alignment above, are the amino acids differing from the known BMP-3 proteins, such as the amino acids differing from the human BMP-3c or reindeer BMP-3c. Preferably the regions containing these amino acids are conserved in a BMP of the present invention. The amino acids 26 and 104 define the region containing amino acids differing from the reindeer BMP-3b counterpart and the amino acids 6 and 138 define the region containing amino acids differing from the human BMP-3b counterpart.

On the other hand, insertions, deletions and substitutions located far outside said characteristic area may not be likely to cause substantial changes in the function, effect or folding of the BMP of the present invention. For example homologues having deletions, such as deletions of few amino acids, preferably 1-10 amino acids, more preferably 1-5 amino acids, most preferably 1-3 amino acids, in carboxyl terminus or amino terminus resulting in shorter polypeptide are in the scope of the present invention as long as said deletions do not affect the characteristic amino acids of the BMP of the invention. It is preferred that said homologues have the advantageous properties of the original reindeer BMP-3c protein, said properties being related to said characteristic amino acids and/or the region around them. Said homologues may have amino acid substitutions which do not substantially affect the function and effect of the protein of the invention. For example an amino acid not located in the active site or near it may be substituted with another amino acid having similar structural and/or chemical properties (e.g. hydrophobic or hydrophilic), i.e. conservative amino acid replacement, as long as said substitution does not substantially alter the function or folding of the mature protein. These kinds of substitutions are well known and understood in the art. Examples of such amino acid properties divided into groups are hydrophobic (Met, Ala, Val, Leu, Ile), neutral hydrophilic (Cys, Ser, Thr), acidic (Asp, Glu), basic (Asn, Gln, His, Lys, Arg), residues that influence chain orientation (Gly, Pro) and aromatic (Trp, Tyr, Phe) amino acids. Substitutions within said groups are generally not likely to cause major changes in the structure of the polypeptide backbone (e.g. a sheet or helical conformation), the charge or hydrophobicity of the molecule or the bulk of the side chain.

The homologues of the BMP of the present invention include for example any known bone morphogenetic protein, such as BMP-3 or counterpart thereof, which contains or has been modified to contain at least part of the conserved amino acids or sequences as described above or corresponding area in a homologous BMP-3 protein in the case the numbering should differ. Also any currently unknown BMP-3c protein from any species modified as described above is in the scope of the invention.

When compared to known reindeer BMP-3b protein, the BMP-3c has one inserted amino acid R26 and five substituted amino acids W30, D31, K75, M76 and V104 calculated from the mature BMP-3c protein as disclosed in SEQ ID NO: 1. When compared to known human BMP-3b protein, the BMP-3c has nine substituted amino acids D6, S11, K27, S66, M76, V95, S109, E133 and Q138 defined from the mature BMP-3c protein as disclosed in SEQ ID NO: 1. These amino acids are characteristic for the BMP of the present invention. However, as E133 and Q138 are located in the carboxy terminal end of the mature protein, they may not play a major role in the function of the protein.

In one embodiment the BMP of the present invention is any BMP-3 containing a consensus sequence of the BMP-3 family. One example of such consensus sequence is the sequence below derived from the following ClustalX alignment wherein several BMP-3 proteins from different species are aligned, said sequence corresponding the amino acids 26-104 of SEQ ID NO: 1. In said consensus sequence the characteristic amino acids of rdBMP-3c differing from known rdBMP-3b (one inserted amino acid R26 and five substituted amino acids W30, D31, K75, M76 and V104) are fixed but other conservative variations among BMP-3 family are allowed.

(SEQ ID NO: 29)
R-K-K-Q-W-D-E-P-R-V/N-C-S/A-R-R-Y-L-K-V-D-F-A-D-I-G-W-N/S-E-W-I-I-S-P-K-S-F-D-A-Y-Y-C-S-G-A-C-E/Q-F-P-M-P-K-M-V/L-R/K-P-S-N-H-A-T-I-Q-S-I-V-R-A-V-G-I/V-V-P/S-G-I-P-E-P-C-C-V

Also other consensus sequences may be defined, for example ones defining an area between amino acids 6-104, 6-109 or 6-138 of SEQ ID NO: 1, or similar sequences differing in length, e.g. by 1-20 amino acids. Such consensus sequences may be defined from the alignment below or similar alignments made by aligning different related BMP proteins. The BMP sequences aligned are from reindeer, human, rat and African clawed frog (Xenopus laevis).

responding area. If there were any insertions or deletions of amino acids in the amino acid sequence of said homologue affecting the numbering, these should be taken into account when defining the location of said essential amino acids, for example by aligning the sequences as described and then defining the locations of said amino acids. However, any of said homologues of the BMP should substantially have the function and efficiency disclosed herein. Because all the known BMP-3 proteins are highly conserved, defining the location of said essential amino acids is unambiguous, such as in the case of human BMP-3b. For example in rdBMP-3b there is a one amino acid deletion when compared to rdBMP-3c, as shown in the alignment above, but still the corresponding amino acids in the compared sequences can be defined easily. Also, said locations can be easily defined also from other BPMs (see the alignment above). Generally such level

```
BMP3C_REINDEER  RKKGQDVFMASSQVLDFDEKTM-                                           (SEQ ID NO: 1)
                QKARKKQWDEPRVCSRRYLKVDFADIGWNEWIISPKSF

BMP3_HUMAN      KKKQRKGPHRKSQTLQFDEQTLKKAR-                                       (SEQ ID NO: 4)
                RKQWIEPRNCARRYLKVDFADIGWSEWIISPKSF

BMP3_RAT        KKKQRKGPHQKGQTLQFDEQTLKKAR-                                       (SEQ ID NO: 5)
                RKQWIEPRNCARRYLKVDFADIGWSEWIISPKSF

BMP3_XENOPUS    KKKLRKGSRQKSQTLQFDEQTLKKARP-                                      (SEQ ID NO: 6)
                KQWNEPRNCARRYLKVDFADIGWSEWIISPKSF

BMP3B_REINDEER  RKKGQDVFMASSQVLDFDEKTMQKA-KKQVGEPRVCSRRYLKVDFADIGWNEWI-           (SEQ ID NO: 2)
                ISPKSF

BMP3B_HUMAN     RKKGQEVFMAASQVLDFDEKTMQKAR-                                       (SEQ ID NO: 3)
                RKQWDEPRVCSRRYLKVDFADIGWNEWIISPKSF

BMP3C_REINDEER  DAYYCSGACEFPMPKMVRPSNHATIQ-
                SIVRAVGIVPGIPEPCCVPDKMSSLGVLFLDENR

BMP3_HUMAN      DAYYCSGACQFPMPKSLKPSNHATIQ-
                SIVRAVGVVPGIPEPCCVPEKMSSLSILFFDENK

BMP3_RAT        DAYYCSGACQFPMPKSLKPSNHATIQ-
                SIVRAVGVVSGIPEPCCVPEKMSSLSILFFDENK

BMP3_XENOPUS    DAYYCSGACQFPMPKSLKPSNHATIQ-
                SIVRAVGVVPGIPEPCCVPEKMSSLSILFLDENK

BMP3B_REINDEER  DAYYCSGACEFPMPRWVRPSNHATIQ-
                SIVRAVGIVPGIPEPCCAPDKMSSLGVLFLDENR

BMP3B_HUMAN     DAYYCAGACEFPMPKIVRPSNHATIQ-
                SIVRAVGIIPGIPEPCCVPDKMNSLGVLFLDENR

BMP3C_REINDEER  NVVLKVYPNMSVETCACQ
m
BMP3_HUMAN      NVVLKVYPNMTVESCACR

BMP3_RAT        NVVLKVYPNMTVDSCACR

BMP3_XENOPUS    NVVLKVYPNMTVESCACR

BMP3B_REINDEER  NVVLKVYPNMSVETCACQ

BMP3B_HUMAN     NVVLKVYPNMSVDTCACR
```

In one embodiment of the present invention said BMP is any BMP or homologue, derivative or fragment thereof comprising the amino acids 26-104 of the SEQ ID NO: 1. Said amino acid locations are calculated from amino terminus of any general mature BMP-3 protein, such as the BMP-3c protein of SEQ ID NO: 1 or a homologue, derivative or fragment thereof, wherein the sequence at the amino terminus begins with RKKGQ, as for example in reindeer (see the sequence alignment above or SEQ ID NO: 1), or at the corof homology may be at least 70%, preferably 80%, more preferably 93% and most preferably 95% at the amino acid level.

In another embodiment the BMP of the present invention is any BMP or homologue, derivative or fragment thereof containing the amino acids 6-104 of the SEQ ID NO: 1. In another embodiment the BMP of the present invention is any BMP or homologue, derivative or fragment thereof containing the amino acids 6-109 of the SEQ ID NO: 1. In another embodiment the BMP of the present invention is any BMP or homologue, derivative or fragment thereof containing the amino acids 6-138 of the SEQ ID NO: 1. In still another embodiment the BMP of the present invention is a BMP-3 protein. In still another embodiment the BMP of the present invention is BMP-3 or homologue, derivative or fragment thereof containing the amino acid sequence of SEQ ID NO: 1. The homologues, derivatives or fragments mentioned in these embodiments shall contain at least one of the characteristic amino acids described above. Said homologues, derivatives or fragments do not include the known BMP-3 proteins as such, such as hBMP-3b or rdBMP-3b, since they do not contain said characteristic amino acids of the BMP-3c of the present invention. However, a known BMP, such as BMP-3, modified to contain at least one of said characteristic amino acids may be considered as such homologue, derivative or fragment.

Another embodiment of the present invention provides the BMP as described above with a heparin binding site (EBS). Generally this is an amino acid sequence capable of binding heparin. In one embodiment said heparin binding site is located at the amino terminus of said BMP, such as before the sequence of SEQ ID NO: 1 or functional homologue thereof. In one embodiment the heparin binding site contains amino acid sequence AKHKQRKRGT (SEQ ID NO: 7) or QAKHKQRKRGT (SEQ ID NO: 8). Said heparin binding site may also be a functional homologue, derivative or fragment thereof. The heparin binding site improves the expression of the recombinant BMP protein and also enhances the biological activity thereof. Further, the heparin binding site significantly helps the expression of recombinant bone morphogenetic proteins in bacterial cells, such as *E. coli*.

One embodiment of the present invention provides a nucleic acid molecule, such as a DNA or RNA molecule, encoding said BMP of the invention. Because of the degeneracy of the genetic code there are a number of different nucleic acid sequences encoding the BMP of the invention. All such nucleic acid variants are in the scope of the present invention. Preferably said nucleic acid molecule is a DNA molecule. Examples of said DNA sequences are disclosed in FIGS. 4-6.

One embodiment of the present invention provides a replicable vector containing the nucleic acid molecule described above in operative association with an expression control sequence thereof. Such vector may be used for producing recombinant BMP of the present invention in a suitable host system.

The nucleic acid encoding the BMP of the invention may be inserted into said replicable vector for cloning or for expression. Various vectors are publicly available. The vector may, for example, be in the form of a plasmid, cosmid, viral particle or phage. The appropriate nucleic acid sequence may be inserted into the vector by a variety of procedures. In general, DNA is inserted into an appropriate restriction endonuclease site(s) using techniques well known in the art. Vector components may include for example one or more signal sequence(s), an origin of replication, one or more marker genes, an enhancer element, a promoter, and a transcription termination sequence. Construction of such suitable vectors containing one or more of these components employs standard ligation techniques which are well-known to a person skilled in the art.

Generally said BMP may be produced recombinantly by expressing in any suitable host cell, such as in a bacterial host cell. Such methods are well-known in the art and they are described in literature. It is essential that the protein is folded properly during the expression and it contains the necessary post-translational modifications.

It is not always possible to express and purify certain proteins properly, for example because of solubility or refolding problems. Usually *E. coli* can not make post-translational modifications typical for mammalian cell systems. However, the inventors of the present invention have produced recombinant reindeer BMP-3c mature part in *E. coli* and after purification and refolding managed to prove it to be in biologically active form.

There are certain benefits when a protein, such as a BMP, is expressed in a bacterial host, such as *E. coli*. The protein generally shows lowered immunogenicity when compared to a similar protein expressed in for example yeast host. This may be useful later when the protein is utilized, for example administered as a medicament. *E. coli* produces proteins without modifications, such as glycosylation. This is particularly useful for proteins for which glycosylation is not a requirement, but which could be a problem if the protein is produced in other systems (e.g. yeast), which can over-glycosylate, or add inappropriate carbohydrates to the protein, which could lead to reduced or no activity of expressed protein and potentially create a risk of immunogenicity (Pedro de Noronha Pissarra: Recombinant DNA Proteins for the Biopharmaceutical Industry and the Future for *Escherichia coli*. Business Briefing: Pharma Outsourcing, London, 2004).

One embodiment of the present invention provides a host cell containing the nucleotide molecule or the nucleotide vector described above. Suitable cells include all prokaryotic and eukaryotic cells which are able to express the protein of the invention. Such host cells are well known in the art and a person skilled in the art can easily choose a suitable one. Another embodiment provides a BMP produced by culturing said cell to express said protein and by recovering said expressed protein from said host cell. Any suitable methods for recovering or isolating the protein may be used and such methods are well known in the art.

The BMP of the invention may be used for treating disorders related to bone, cartilage, tendon or periodontal defects or diseases or the like wherein regeneration, repair or growth thereof is desired, or other diseases. The protein of the invention may also be used to heal wounds, such as burns, incisions and ulcers, and to related tissue repair and also for treatment of cancer, as disclosed in EP 1131087.

Since BMP proteins generally lack species specificity, the patient suffering from said defect may be any suitable animal, preferably mammal, such as human, and the BMP protein used for treatment may be of any suitable origin. The use of related BMP proteins for several types of therapeutical applications is well known in the art (see e.g. U.S. Pat. No. 6,245,889 and WO 98/51354).

"Disorders related to bone, cartilage, tendon or tooth defects" as used herein refers generally to any known disorder wherein bone, cartilage, tendon or periodontal healing or reconstruction, i.e. regeneration, is desired. Non-limiting examples of treatments of disorders related to bone, cartilage, tendon or periodontal defects or diseases or the like are regeneration, repair and growth of bone and periodontal tissue; regeneration, repair and growth of bone in mammals, such as human; treatment of abnormalities of bone formation or regeneration; wound healing, ectopic bone induction and healing of segmental bone defects in vertebrates; treatment of skeletal disorders and deformations; repair of large bone defects originating from trauma, excision of tumors or congenital malformations, reconstructing bone stocks worn off by an implanted endoprothesis in revision operations and healing delayed or non-united fractures; repair of bone and cartilage defects such as critical size defects, non-critical size defects, non-union fractures, segmental non-union of fractures; acute fractures, chondral defects, osteochondral defects, subchondral defects; local bone and cartilage formation; defects resulting from degenerative diseases; dental applications such as repair of periodontal tissues, alveolar bone, cementum, tooth root membrane, filling of the tooth root canal and improvement or enhancement of fixation of the dental implant. Examples of such disorders can be found in Ann Rheum Dis, Volume 62, 2003, 73-78: Reddy A H: Cartilage morphogenetic proteins: role in joint development, homeostasis and regeneration.

Other diseases wherein the BMP of the present invention is useful are for example cancer, especially lung cancer, fibromyalgia, psoriasis and other dermatological disorders, and rheumatic disorders and the like. Examples of such cancers and methods and compositions for treating thereof are disclosed in EP 1131087.

In one embodiment the BMP of the present invention, such as BMP-3, may be provided, in any application described herein, together with one or more additional morphogenetic proteins, such as another BMP protein species or the like. Generally this provides a synergetic effect, as it is known in the art. Examples of other suitable BMP proteins are, but are not limited to, BMP-1, BMP-2, another BMP-3, BMP-4, BMP-5, BMP-6, BMP-7 and BMP-8. Also other therapeutically useful agents may be provided, such as epidermal growth factor, fibroblast growth factor and transforming growth factors (U.S. Pat. No. 6,245,889). In one embodiment said additional morphogenetic protein is originated from reindeer, such as any other reindeer BMP protein. In one embodiment the BMP of the present invention is provided as a dimer, as a homodimer or as a heterodimer together with another BMP protein as described above. In still another embodiment the BMP as a dimer or together with another factor or protein, as described above, is used for manufacturing medicament for treating disorders described in the specification.

In one embodiment of the present invention an osteogenic device, such as an implant, is provided containing the BMP of the invention. The osteogenic device may contain a biocompatible matrix, such as a calcium phosphate, carboxy methyl cellulose or collagen matrix or combinations thereof. In one embodiment said calcium phosphate matrix is a hydroxyapatite matrix. Said matrix may provide slow release of the BMP protein and/or the appropriate environment for presentation of the BMP protein. The osteogenic device may also contain a metal implant surrounded by said biocompatible matrix. One example of said metal is titanium. Some examples of such osteogenic devices are disclosed in WO 98/51354.

Non-limiting examples of the different framing materials, carriers or frames for forming e.g. different kinds of osteogenic devices or the like with the protein of the present invention are a medium in the form of powder, sponge, strip, film, gel, web or solution or suspension; semi-solid liquid carrier suitable for intramuscular, intravenous, intramedullary or intra-articular injection; isolated mesenchymal stem cells; any pharmaceutically acceptable vehicle; crusted auto- or allograft; any pharmaceutically acceptable matrix; a material selected from the group comprising hydroxyapatite, collagen, polymers (e.g. polylactic acid, polyglycolic acid), synthetic polymers, hyaluronic acid, α-BSM, calcium phosphate, tricalcium phosphate, aporous ceramic biopolymers, aporous resorbable biopolymers, coral, demineralized bone, bioglass, any biodegradable material and combinations thereof; binding agents selected from the group comprising mannitol, dextrans, white petrolatum, alkyl and methyl celluloses, wetting agents such as sodium salt, fobrin glue, mammalian fibrinogen and thrombin and combinations and admixtures thereof. The osteogenic device may be for example a structurally stable, three dimensional implant in form of a cube, cylinder or block or in the shape of an anatomical form or an injectable form. Examples of osteogenic devices, useful materials and techniques are disclosed in book "Skeletal reconstruction and bioimplantation" (T. Sam Lindholm, 1997, Springer-Verlag, Heidelberg, Germany).

In one embodiment of the present invention a pharmaceutical composition is provided containing a therapeutically effective amount of BMP of the invention together with a pharmaceutically acceptable vehicle or carrier. Said pharmaceutical compositions may be used for treating disorders related to bone, cartilage, tendon or periodontal defects or diseases, wounds and other tissue defects or any other disorders described herein.

One embodiment of the present invention provides a method for inducing the formation of bone, cartilage, tendon, tooth or the like wherein said bone, cartilage, tendon, tooth or the like is treated with the BMP of the invention or combinations thereof as described above, in vitro or in vivo. Still another embodiment of the invention provides a method for treating disorders described in the specification comprising administering the isolated BMP of the present invention to a patient suffering from said disorders. Said BMP may be administered as a pharmaceutical composition or as an osteogenic device described above. Further morphogenetic proteins or other useful agents may be administered together with said BMP of the invention, as described above, to enhance the therapeutical effect.

In the following description and examples it is described how recombinant reindeer BMP-3c mature part with and without heparin-binding site (HBS) according to embodiments of the present invention was produced in *E. coli*. After purification and refolding the osteoinductive activity was verified by bioassay in mouse tight muscle pounches. The in vivo bioassay is a standard method used for assaying BMP activity since its discovery. It includes implantation of BMP in the hindquarter muscle of a mouse and estimation of heterotopic new bone induction after 10-21 days by radiology and histology.

The osteoinduction was observed in all four study groups (1 mg, 3 mg, 5 mg and 8 mg of recombinant reindeer BMP-3c) and it was increased in dose dependent manner (Table 3).

TABLE 3

Comparison of the osteoinduction responses of reindeer BMP-$3c_{138}$ and BMP-$3c_{110}$ proteins with different doses

| | BMP-$3c_{138}$ | | | |
|---|---|---|---|---|
| Dose | 1 mg | 3 mg | 5 mg | 8 mg |
| Reindeer | ☐ ☐ ☐ ☐ | + - ++ ☐ | (+) + + + | (+) ☐ ☐ ☐ |

| | BMP-$3c_{110}$ | | | |
|---|---|---|---|---|
| Dose | 1 mg | 3 mg | 5 mg | 10 mg |
| Reindeer | ☐ ☐ ☐ ☐ | - + (+) + | ++ ++ + - | + + ++ ++ |

Figure 7:
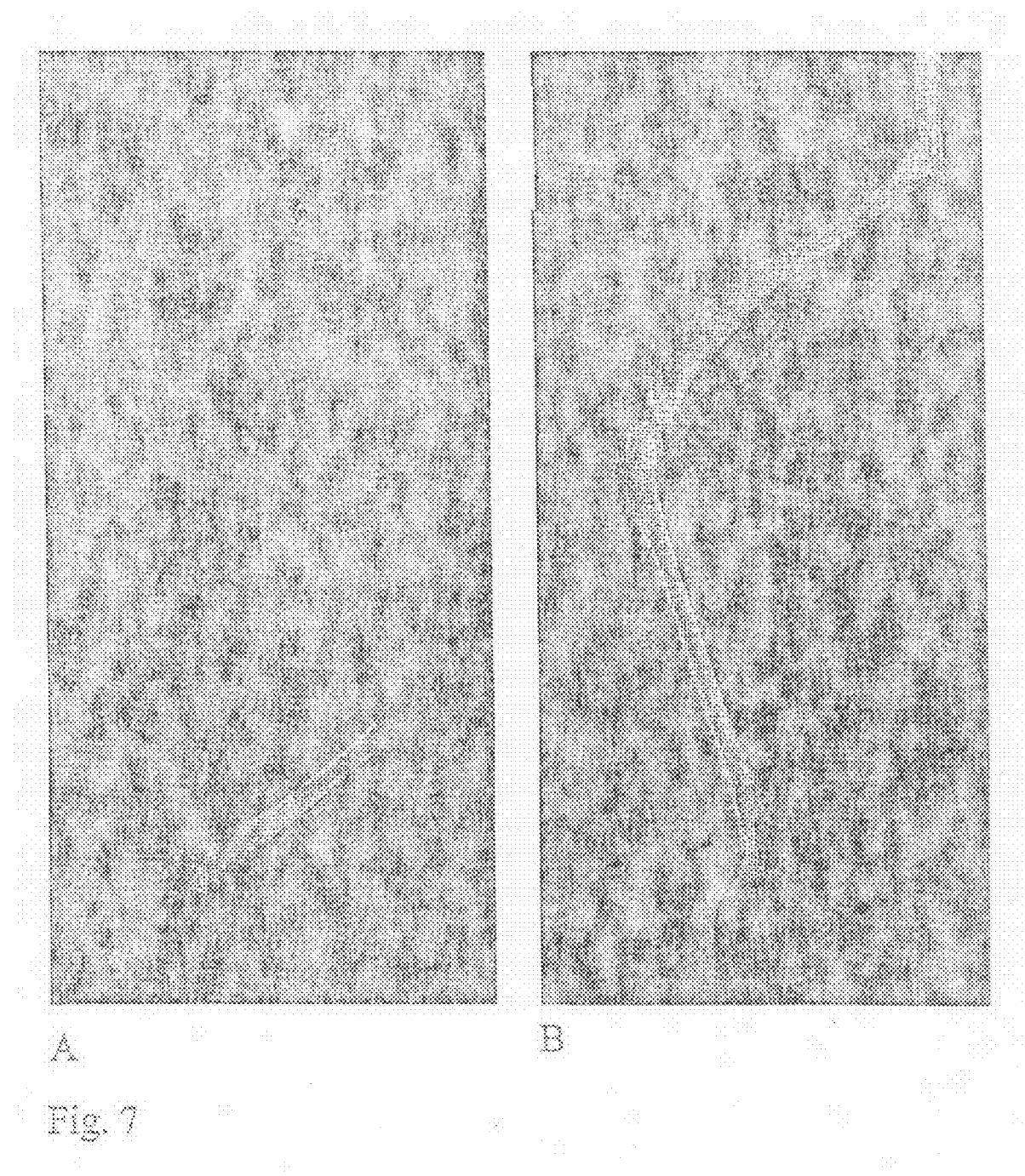
FIG. 7 shows X-ray images of a mouse hindquarter muscle: A) reference and B) implanted with BMP-3c of the present invention.

The results of the in vivo bioassay are shown in FIG. 7. FIG. 7A is a reference and 7B is a sample implanted with BMP-3c of the present invention. The bioassay was carried out as described in Marshall R. Urist, J. J. Chang, A. Lietze, Y. K. Huo, A. G. Brownell and R. J. DeLange (1987): Preparation and Bioassay of Bone Morphogenetic Protein and Polypeptide Fragments, Methods Enzymol 146: 294-312.

There were great difficulties to get recombinant rdBMP-3c mature part expressed in *E. coli* TOP10. Therefore, the inventors assumed that poor expression was caused by the high GC-content in N-terminal region of the mature part of rdBMP-3c. Because heparin binding site (HBS), existing in the beginning of the reindeer BMP-2 mature part, is coded by nucleotide sequence with low GC-content, a construct in which this HBS sequence was added in front of the rdBMP-3c mature part sequence was created and this way the inventors managed to improve the expression of recombinant.

HBS located in the N-terminus of rdBMP-2 contains 10 basic amino acid residues and is reminiscent of known or postulated heparin-binding sites in other growth factors. It is also possible that the interaction between protein with HBS and extracellular matrix might have an important effect on the establishment of morphogenetic gradients during development by limiting the free diffusion of a protein. Therefore, it was assumed that HBS could also improve the biological activity of recombinant rdBMP-3c by prolonging the duration of disappearance of protein from the implantation site.

EXAMPLES

Cloning of cDNA of Reindeer BMP-3c and Homology Comparison Analysis

PCR product around 400 bp was isolated and cloned into pGEM-T® vector. The nucleotide sequence obtained from ABI Prism reactions was analyzed with computer and it was compared to already known human BMP sequences. Due to homology searches the newly cloned cDNA seemed to be more homologous with human BMP-3b (nucleotide homology 89% and amino acid homology 93%) as compared to human BMP-3 (nucleotide homology 69% and amino acid homology 81%). When compared to all known BMPs the newly cloned cDNA seemed to be most homologous with reindeer BMP-3b (nucleotide homology 96% and amino acid homology 95%). Therefore the cDNA of the present invention was named reindeer BMP-3c.

Expression of Reindeer BMP-3c Mature Part in TOP10, Rosetta and Origami *E. coli* Cells In previous studies human BMP-3 has been produced in CHO cells, in *E. coli* cells and using retroviral system. Furthermore, human BMP-3 and rat BMP-3b have been produced as recombinant proteins using adenoviral system. Nevertheless, not any member of BMP-3 subfamily of deer animal origin has been produced as recombinant protein.

The 414 nucleotide corresponding 138 amino acid long mature part of reindeer BMP-3c was subcloned from pGEM-T® into pTrcHis2A vector and the expression of the recombinant protein in *E. coli* TOP 10 (Invitrogen) was analyzed, but no induction was observed. It was concluded that this could possibly be caused by high GC content in the beginning of the rdBMP-3c. It was also noticed that heparin binding site existing in the beginning of reindeer BMP-2 mature part had very low GC content and by adding it in front of reindeer BMP-3c mature part it could also be utilized as a part of the purification procedure. Therefore, the mature part of BMP-3c/138 and BMP-3c/110 were cloned into pTrcHBS vector and pTrcHBSBMP-3c/138 and pTrcHBSBMP-3c/110 were obtained. Successful induction of both recombinant HBSrdBMP-3c/138 and HBSrdBMP-3c/110 was verified by SDS-PAGE and the expression level was high.

To achieve protein expression of reindeer BMP-3c/138 and BMP-3c/110 proteins, another protein expression system was tested. Therefore pET22b(+) with His6-tag and pelB leader was chosen as new expression vector system. pETrd3c/138 and pETrd3c/110 vectors were constructed. Rosetta (DE3) (Novagen) and Origami B (DE3) (Novagen) *E. coli* lines were used for expression. Successful IPTG inductions of recombinant rdBMP-3c with both constructs were verified by SDS-PAGE.

Biological Activity of Recombinant Reindeer BMP-3c/138 and BMP-3c/110

When produced in CHO cells or *E. coli* system recombinant human BMP-3 has shown osteogenic activity in bioassay, but when retroviral and adenoviral systems were used to produce recombinant human BMP-3 no osteogenic function was observed. Using adenoviral vector system, BMP-3b has been observed to act in synergetic manner with BMP-2 in bone formation procedure but it failed to cause bone induction on its own. Nevertheless, BMP-3 of deer animal origin (Cervidae family) has not been even cloned and earlier cloned BMP-3b of reindeer origin has not been tested for its biological activity.

In this study it is showed that new member of BMP-3 subfamily, recombinant reindeer BMP-3c, produced in *E. coli* cells cause new bone formation when implanted in mouse tight muscle pouches with collagen sponge.

Example 1

Cloning and Sequencing of 3'-part of the cDNA of Reindeer BMP-3c

A. RNA Isolation

The antlers of a 3-year-old male reindeer were cut off and frozen in liquid nitrogen immediately after slaughtering. The frozen antlers were cut in 0.5 cm slices and stored at −70° C. Reindeer antler mRNA was isolated using the QuickPrep® Micro mRNA Purification Kit (Pharmacia Biotech). A part of the reindeer antler slice was cut in small pieces (about 1 $mm^3$) and 0.1 g of this tissue was added to 0.6 ml of Extraction Buffer containing guanidinium thiocyanate and N-lauroyl sarcosine. The tissue was homogenized with Ultra Turrax for 3 times 10 seconds on ice and cooled between every homogenization. 1.2 ml of Elution Buffer was added and suspension was further homogenized for 1 time 10 seconds. A uniform suspension was obtained.

The reindeer antler homogenate and Oligo(dT)-Cellulose were centrifuged at top speed [14,000 rpm, RT, Centrifuge 5415 C (Eppendorf)] for 1 minute. The buffer from the Oligo (dT)-Cellulose pellet was removed and the cleared tissue homogenate was placed on the top of it. The tube was inverted to resuspend the Oligo(dT)-Cellulose pellet. The suspension was gently mixed for 5 minutes and centrifuged at top speed [14,000 rpm, RT, Centrifuge 5415 C (Eppendorf)] for 10 seconds. The supernatant was discarded.

Oligo(dT)-Cellulose was resuspended in High-Salt Buffer [10 mM Tris-HCl (pH 7.5), 1 mM EDTA, 0.5 M NaCl] and suspension was centrifuged at top speed [14,000 rpm, RT, Centrifuge 5415 C (Eppendorf)] for 10 seconds. Washings with High-Salt Buffer were repeated for 5 times and 2 additional times with Low-Salt Buffer [10 mM Tris-HCl (pH 7.5), 1 mM EDTA, 0.1 M NaCl]. 3 ml Low-Salt Buffer was added and suspension was transferred to MicroSpin Column. The MicroSpin Column was placed in Eppendorf tube and centrifuged at top speed for 5 seconds. Oligo(dT)-Cellulose in the column was rinsed for 3 times with Low-Salt Buffer.

The reindeer antler mRNA was eluted to a clean Eppendorf tube from the MicroSpin Column by adding 0.2 ml 65° C. Elution Buffer (QuickPrep® Micro mRNA Purification Kit, Pharmacia Biotech) to the column and centrifuging at top speed [14,000 rpm, RT, Centrifuge 5415 C (Eppendorf)] for 5 seconds. The elution step was repeated twice. The isolated mRNA was precipitated by adding 5 µl of glycogen solution (5-10 mg/ml in DEPC-treated $H_2O$), 1/10 volume K Acetate solution (2.5 M potassium acetate, pH 5.0) and 0.5 ml absolute ethanol (chilled to −20° C.) to each elution. Precipitation was allowed to occur at −20° C. for at least 30 minutes and mRNA was centrifuged at top speed [14,000 rpm, 4° C., Centrifuge 5415 C (Eppendorf)] for 5 minutes. Precipitated mRNA was stored at −70° C. until cDNA synthesis was performed.

B. cDNA Synthesis

Reverse transcription of the reindeer antler mRNA was performed by modifying the instructions of the Time Saver™ cDNA Synthesis Kit (Pharmacia Biotech). 3 µg of mRNA was heat-denatured at 65° C. for 10 minutes and chilled on ice. 0.2 µmol DTT, 0.5 µg Oligo(dT)$_{12-18}$ Primer and heat-denatured mRNA were added to First strand reaction mix containing FPLCpure™ Cloned Murine Reverse Transcriptase, RNAguard™, RNase/DNase-Free BSA, dNTPs (dATP, dCTP, dGTP and dTTP) in aqueous buffer (Time Saver™ cDNA Synthesis Kit, Pharmacia Biotech). The mixed solution was incubated at 37° C. for 1 hour. After the incubation, the First strand reaction mix was added to the Second strand reaction mix containing *E. coli* RNase H and *E. coli* DNA polymerase I and dNTPs in aqueous buffer (Time Saver™ cDNA Synthesis Kit, Pharmacia Biotech). The solution was mixed gently and incubated in RT for 30 minutes. The synthesized cDNA was stored at 4° C.

C. Screening of Reindeer Antler cDNA

The part of the cDNA of the reindeer BMP-3c was amplified by PCR (Polymerase chain reaction) method using degenerative primers (5'-CGCAA(A/G)GACCGCA(A/G)GAAGAA(A/G)GGC -3') (SEQ ID NO: 9) and (3'-TC(T/C)GT(A/G)GAGACCTGTGCCTG(T/C)CAA-5') (SEQ ID NO: 10) designed on the basis of homology of already known BMP-3b genes of the different mammalian species (human, rat and mouse). In addition to 100 ng of reindeer antler cDNA and 40 pmol of each primers the 50 pl of PCR reaction mixture contained 0.4 mM dNTPs (PCR Core Kit, Roche) and 0.7 U/µl Expand High Fidelity enzyme mix (thermostable Taq polymerase+proofreading polymerase, Roche) in Expand High Fidelity buffer with MgCb (Expand High Fidelity PCR System, Roche). The reaction was performed under the following program using Mastercycler personal apparatus (Eppendorf) : initial denaturation at 94° C. for 4 minutes and 25 cycles of denaturation 94° C. for 1 minute, annealing of the primers 55° C. for 1 minute, elongation of DNA strands 72° C. for 2 minutes. The final extension was performed at 72° C. for 10 minutes.

D. Cloning into pGEM®-T Vector

The PCR products were purified straight from the PCR reaction mix by Wizard® PCR Preps DNA Purification System (Promega) and ligated into the pGEM®-T vector (FIG. 1) by T4 DNA Ligase (pGEM®-T Vector System I; Promega). 0.3 µg of purified PCR product and 2.3 µg/ml of pGEM®-T vector were added to ligation buffer containing 18 mM Tris-HCl (pH 7.8), 6 mM $MgCl_2$, 6 mM DTT, 0.3 mM ATP, 3% polyethylene glycol and 0.14 U/µl T4 DNA Ligase in total volume of 66 µl. The reaction was allowed to occur at +16° C. water bath which was allowed to cool to +4° C. overnight. The newly formed plasmid was named as pGEMrd3c/142 (FIG. 1).

E. The Production of Competent *Escherichia coli* TOP10 F' Cells

The competent *Escherichia coli* TOP10 F' cells were produced by the calcium chloride/magnesium chloride procedure. 2 ml of LB-medium was inoculated with *E. coli* TOP10 F' cells and grown overnight at 37° C. with shaking (225 rpm). Next morning 100 ml of fresh LB medium was inoculated with 1 ml of overnight culture and the culture was grown at 37° C. with shaking (225 rpm) to an $OD_{600}$ of 0.5-0.6. The cultured cells were collected by centrifugation (2500×g, 5 min), resuspended in 10 ml of 0.1 M $MgCl_2$ solution and collected again by centrifugation (2500×g, 5 min). After the $MgCl_2$ treatment the cells were resuspended in 10 ml of 0.1 M $CaCl_2$ solution, incubated in ice bath for 30 minutes and recollected by centrifugation (2500×g, 5 min). The $CaCl_2$ treatment was repeated except that in the second time 3.5 ml of $CaCl_2$ was used and the incubation time was 1 hour. Glycerol was added to suspension to final concentration of 14% (v/v) and the solution was divided into 200 µl portions. The competent *E. coli* TOP10 F' cells were frozen in liquid nitrogen and stored at −70° C.

F. Transformation of the Competent *Escherichia coli* TOP10 F' Cells and Selection of Clones Containing Reindeer BMP-3c The competent *Escherichia coli* TOP10 F' cells were melted in ice bath for 15 minutes. 20 µl of ligation mix (described above) was added to 100 µl of TCM (10 mM Tris-HCl, 10 mM $CaCl_2$, 10 mM $MgCl_2$, pH 7.0) and mixed with 200 µl of the competent *E. coli* cells. The mixture was incubated in ice bath for 30 minutes before the heat shock (43° C., 3 minutes). After the heat shock 800 µl of LB medium was added and the cells were allowed to regenerate for 30 minutes at 37° C. The transformed cells were collected by centrifugation at top speed for 2 minutes and resuspended to 30 µl of growth medium. The cell suspension was plated to two LB plates containing 25 µg/ml ampicillin covered with 1 mmol IPTG (isopropyl-β-D-thiogalactopyranoside) and 2.4 nmol X-gal (5-bromo-4-chloro-3-indolyl-β-D-galactoside) and the cells were grown at the plates overnight at 37° C. The positive clones were recognized by blue color formation based on α-complementation of lacZ gene. The method is described in detail in Sambrook and Russel (2001), Molecular Cloning, Cold Spring Harbor Laboratory Press, New York.

G. Isolation of pGEMrd3c Plasmids and Sequencing of cDNA Inserts

The plasmids were isolated by Wizard® Plus Minipreps DNA Purification System (Promega) and then further purified by ethanol precipitation. The cDNA identity was confirmed by sequencing with ABI Prism (Perkin-Elmer Corporation). The sequencing reaction was performed using DYEnamic ET Terminator Cycle Sequencing Kit (Amersham Pharmacia Biotech) and Mastercycler Personel apparatus (Ep- pendorf). The primers in the PCR reaction for sequencing were (5'-TAATACGACTCACTATAGGGCGA-S') (SEQ ID NO: 11) and (3'-ATTTAGGTGACACTATA-GAATAC-5') (SEQ ID NO: 12) and the program was as follows: 25 cycles of denaturation 94° C. for 30 seconds, annealing 50° C. for 15 seconds, elongation for 60° C. The amplified PCR products were precipitated by ethanol precipitation method. In 10 µl reaction 1 µl of 1.5 M Na-acetate −250 mM EDTA buffer and 95-100% ethanol was added so that the final ethanol concentration was 75%. The precipitation was allowed to occur in ice bath for 7 minutes and then the mixture was centrifuged for 20 minutes. The supernatant was discarded and the pellet was washed with 125 µl of 70% ethanol in RT. The solution was centrifuged briefly and the washing ethanol was removed as precisely as possible. The pellet was dried in 37° C. for a few minutes until all the ethanol was completely fumed. The ABI Prism apparatus was located in Department of Medical Biochemistry and Molecular Biology, University of Oulu, Finland and the final sequencing was performed there. The nucleotide sequence and the corresponding amino acid sequence of partial cDNA of reindeer BMP-3c is seen in FIG. 6.

Example 2

Expression of the Recombinant Reindeer BMP-3c Mature Part in *Escherichia coli* TOP10 F', Origami B (DE3) and Rosetta (DE3) Cells A. Amplification of the Mature Part of Reindeer BMP-3c for Expression Vector The mature part of reindeer BMP-3c was amplified from the pGEM3c/142 plasmid by PCR method using homology primers (5'-GGATCCGAGGAA-GAAGGGCCAGGAT-GTTTTC-3') (SEQ ID NO: 13) and (3'-AAGCTTTTG-GCAGGCA-CAGGTCTCCAC-5') (SEQ ID NO: 14) (see Example 2 Part B). There were recognition sites for restriction enzymes Bam HI and Hind III at the 5'- and 3'-end of primers respectively.

In addition to 0.05 µg of pGEMrd3c/142 plasmid and 40 pmol of each primers the 50 µl of PCR reaction mixture contained 0.4 mM dNTPs (PCR Core Kit, Roche) and 0.7 U/µl Expand High Fidelity enzyme mix (thermostable Taq polymerase+proofreading polymerase, Roche) in Expand High Fidelity buffer with MgCb (Roche). The PCR reaction was performed under the following program using Mastercycler personel apparatus (Eppendorf): initial denaturation at 94° C. for 4 minutes and 25 cycles of denaturation 94° C. for 1 minute, annealing of the primers 55° C. for 1 minute, elongation of DNA strands 72° C. for 2 minutes. The final extension was performed at 72° C. for 10 minutes. The PCR product was purified directly from the PCR reaction mixture using Wizard® PCR Preps (Promega) and ligated to the pGEM®-T vector. The newly formed plasmid with the mature part of the reindeer BMP-3c was named as pGEMrd3c/138 (FIG. 1).

B. Subcloning of the Mature Part of Reindeer BMP-3c from pGEM®-T Vector to the Expression Vector pTrcHis 2A (Invitrogen) and Transformation of the Competent *Escherichia coli* TOP10 F' Cells The subcloning of the mature part of reindeer BMP-3c from pGEMrd3c/138 to the expression vector pTrcHis 2A (FIG. 2) was accomplished by first digesting the mature part off from pGEMrd3c/138 using Bam HI and Hind III restriction enzymes and then ligating the insert to pTrcHis 2A digested with the same enzymes. The Bam HI (Roche) and Hind III (Roche) digestion of pGEMrd3c/138 and pTrcHis 2A (1 µg) was performed in 10 µl of 10 mM Tris-HCl, 10 mM NaCl, 5 mM $MgCl_2$, 1 mM 2-mercaptoethanol, pH 8.0 (SuRE/Cut Buffer B, Roche) with 1 U/µl of each restriction enzyme. The reaction was allowed to occur for 1.5 hours in 37° C. and then the restriction enzymes were inactivated by heating in 65° C. for 20 minutes and freezing in −20° C. Ligation was performed in 2× Rapid Ligation Buffer (supplied with pGEM®-T vector by Promega) in +16° C. water bath which was allowed slowly to cool down to +4° C. overnight (ligase concentration 0.1 U/µl).

Figure 2:
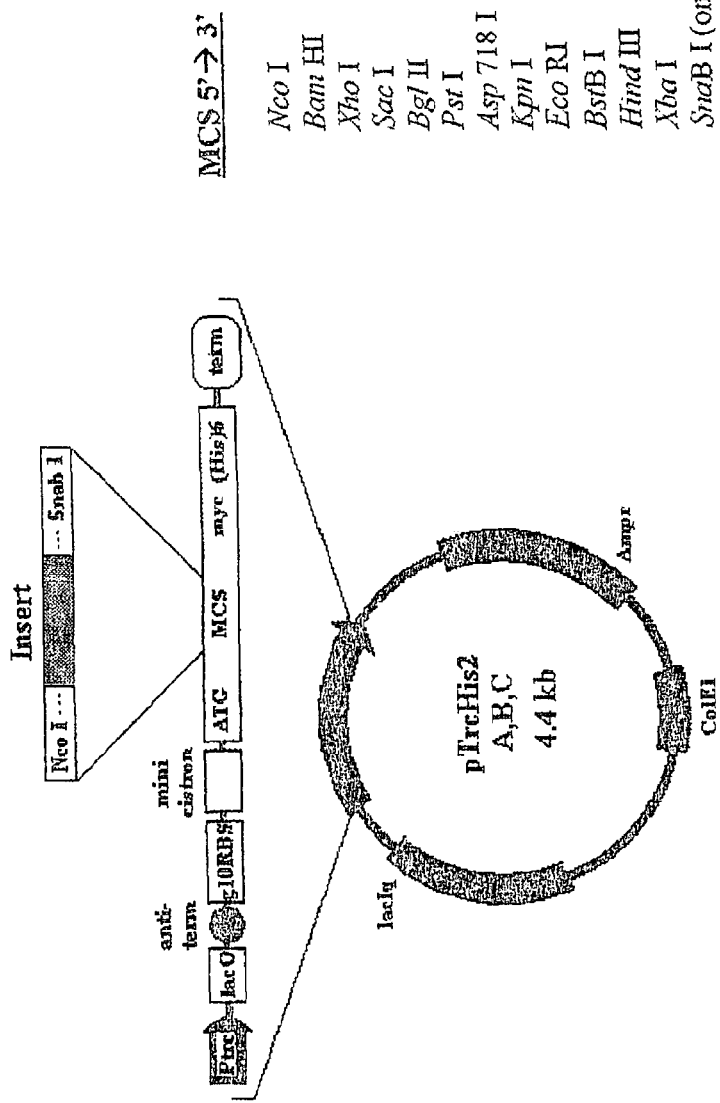
FIG. 2 shows plasmids containing rdBMP-3c inserts in expression vector pTrcHis2 (Invitrogen).

The newly formed construct was checked by sequencing (protocol is described in Example 1 Part G) using primers (5'-AGAGGTATATATTAATGTATCG-3') (SEQ ID NO: 15) and (3'-ATGGTCGACGGCGCTATTCAG-5') (SEQ ID NO: 16). Expression vector containing pTrcHis 2A plus the reindeer BMP-3c mature part cDNA was named as pTrcrd3c (FIG. 2). The competent Escherichia coli TOP10 F' cells were transformed with pTrcrd3c as described in Example 1 Part F.

C. Insertion of the mature part of reindeer BMP-3c to the expression vector pET22b(+) (Novagen) and transformation of the competent Escherichia coli Origami B (DE3) and Rosetta (DE3) cells.

Figure 3:
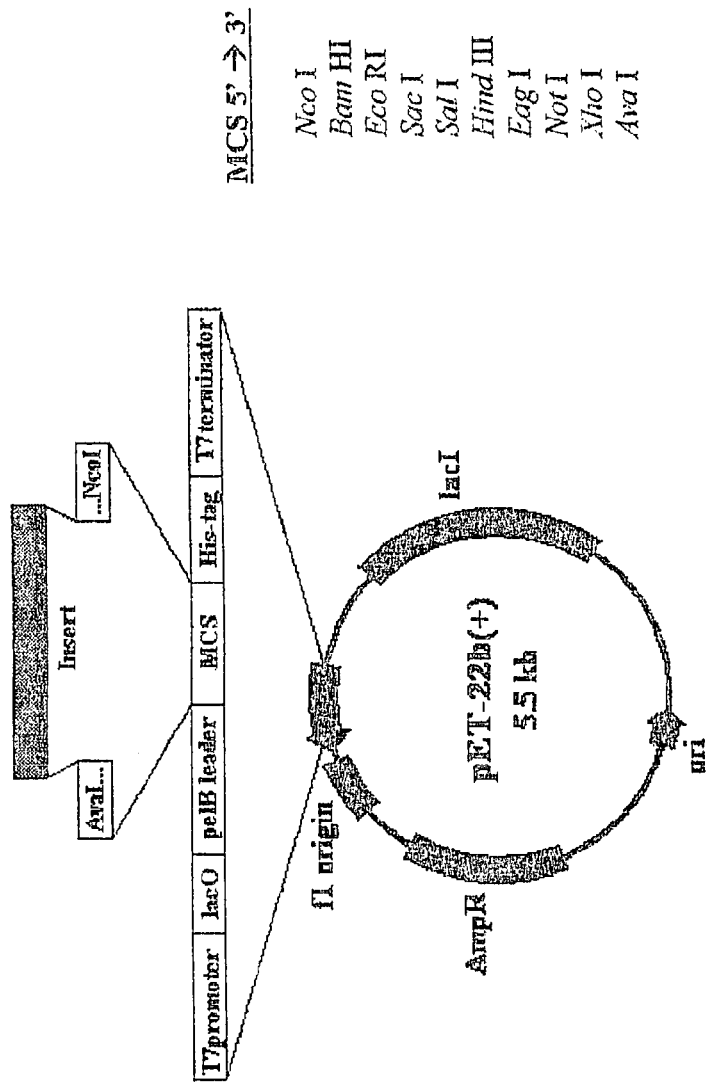
FIG. 3 shows plasmids containing rdBMP-3c inserts in expression vector pET-22b(+) (Novagen).

The subcloning of the mature part of reindeer BMP-3c to the expression vector pET22b(+) (Novagen) (FIG. 3) was performed as described above (see Example 2 Part B). The newly formed plasmids containing pET22b(+) plus the reindeer BMP-3c mature part cDNA was checked by sequencing using primers (5' GGATCCGAGGAAGAAGGGCCAG-GATGTTTTC-S') (SEQ ID NO: 17) and (3'-CG-CAAGCTTTTGGCAGGCACAGGTCTCCAC-5') (SEQ ID NO: 18) (see protocol described in Example 1 Part G) and named as pETrd3c (FIG. 3). Transformations of Origami B (DE3) and Rosetta (DE3) cells were performed following the instructions of the user manual shipped with the competent cells (Novagen).

D. Expression of the Recombinant Reindeer BMP-3c Mature Part in *Escherichia coli* Cell Cultures and Collection of the Cells

*E. coli* cells [TOP10, Origami B (DE3) or Rosetta (DE3)] containing either pTrcrd3c or pETrd3c plasmids were grown overnight in 50 ml of SOB medium containing ampicillin (100 µg/ml) and for Rosetta (DE3) cells also chloramphenicol (34 µg/ml) in +37° C. with shaking (225 rpm). Next morning 1200 ml of SOB medium, containing antibiotics mentioned above, was inoculated with 24 ml of overnight culture and incubated in +37° C. with shaking (225 rpm) until $OD_{600}$ was 0.6 when the cells were in mid-log phase. At this point the recombinant protein expression was induced by adding IPTG to final concentration 1 mM. After the induction the cells were grown additional 4 to 5 hours and then collected by centrifugation. The amino acid sequences of the recombinant proteins produced with respective nucleotide sequences are presented in FIG. 4 (pTrcrd3c) and FIG. 5 (pETrd3c).

Example 3

Purification and Refolding of Recombinant Reindeer BMP-3c Mature Part

A. Washing of Inclusion Bodies

Collected cells were suspended in 50 mM Na-phosphate buffer (pH 7.0, 220 g cells/1 liter of buffer) by shaking. Suspension was centrifuged in 5500×g for 45 minutes in +4° C. Washing with Na-phosphate was repeated once. Cell pellet was weighted and stored in −70° C. overnight. Frozen pellet with partly erupted cells was thawed and suspended in 20 mM Tris-HCl buffer with 0.5 mM EDTA (pH 8.5, 25 mg/ml) by shaking 2 minutes. Suspension was centrifuged 26,000×g for 40 minutes in +4° C. and Tris-HCl-EDTA washing was repeated once. The remaining pellet was weighted. In last washing step, pellet was suspended (200 rpm/minute, overnight, RT) in lysis buffer 6 M GuHCl—20 mM Na-phosphate—0.5 M NaCl (pH 8.0, 35 mg/ml) when all the remaining intact *E. coli* cells are erupted and inclusion bodies made soluble. Suspension was centrifuged (26,000×g, 45 min, RT), pellet discarded and recombinant protein in soluble form in remaining supernatant. Finally, to be sure to get rid of all cell remnants, supernatant was filtered through 45 µm filter.

B. Precipitation According to Isoelectric Point (pI)

The recombinant reindeer BMP-3c expressed from pETrd3c in *Escherichia coli* Origami B (DE3) or Rosetta (DE3) cells was precipitated by isoelectric precipitation in pH 9.54 (pETrd3c/138) and pH 6.35 (pETrd3c/110). Isoelectric point was determined by computer calculations according to amino acid sequence of the recombinant reindeer BMP-3c (FIG. 5). The precipitant was collected by centrifugation (12 000×g, 30 min, RT) and resuspended in lysis buffer (6 M GuHCl—20 mM Na-phosphate—0.5 M NaCl; pH 8.0).

C. Immobilized Metal Affinity Chromatography (IMAC)

In IMAC method, pre-packed HiTrap Chelating HP affinity columns (Amersham Pharmacia Biotech) were used. Columns were charged with $Co^{2+}$-, $Cu^{2+}$- or $Ni^{2+}$-ions according to instruction manual applied by supplier. After column charging, filtered supernatant from washing steps was applied in column. Majority of impurities was removed by washing the column with lysis buffer (6 M GuHCl—20 mM Na-phosphate—0.5 M NaCl, pH 8.0) 5-10 times the bed volume. Second washing was performed with 5-10 times bed volume of buffer in which 6 M GuHCl of lysis buffer was replaced by 6 M Urea. Recombinant reindeer BMP-3c was eluted from the HiTrap column by pH gradient from pH 7.0 to pH 4.0 (6 M Urea—20 mM Na-phosphate—0.5 M NaCl). The fractions were analyzed by SDS-PAGE and the ones containing approximately pure recombinant rdBMP-3c were combined for refolding.

D. Refolding of Recombinant rdBMP-3c Mature Part

The BMP-3c fractions analyzed by SDS-PAGE were pooled and dialyzed against water. After dialysis precipitated protein was collected by centrifugation and resuspended in 8 M Urea, 0.1 M Tris/HCl, pH 8 in the presence of 100 mM DTT, 1 mM EDTA and incubated for 2 h at 25 degrees. The pH was lowered to pH 3-4 by drop wise addition of 1 M HCl. The DTT was removed completely by dialysis against 6 M urea, 10 mM HCl for 2 h at 25 degrees. Dialysis was continued at 4° C. overnight against 6 M urea. Refolding of recombinant rdBMP-3c was performed by two-step dialysis. The first dialysis solution was 20 mM Tris-HCl—150 mM NaCl—3 M urea (pH 7.5). The dialysis water was changed at least six times during two to three days. Desalted sample was centrifuged and pellet was dried by lyophilization. At that point the purity of BMP-3c was 75% and its refolding measured by non-reducing SDS-PAGE was 50%. Quantification of the refolded dimer of recombinant reindeer BMP-3c on Coomassie Brilliant Blue stained gels was done densitometrically.

Example 4

Addition of Heparin Binding Site in Front of the Mature Part of the Reindeer BMP-3c/138 and BMP-3c/110

A. Addition of Heparin Binding Site Coding DNA Fragment to pTrcHis 2A Vector

Two complementary primers seen in Table 4 were designed using heparin binding site (HBS) of the reindeer BMP-2 as a model. Bam HI and Kpn I restriction sites were added in 5' and 3' ends of HBS, respectively. The primers were first denatured in +100° C. for 5 min and then annealed by allowing a small +100° C. water bath to cool down to room temperature and further to +4° C. (1 h). Both annealed HBS fragment (1 µg) and pTrcHis 2A vector (0.5 µg) were digested by Bam HI (1 U/µl) and Kpn I (2 U/µl) in Multi-Core buffer (Promega) in +37° C. for 1.5 hours and ligated in +16° C. water bath which was allowed to cool down to +4° C. overnight. The newly formed construct was checked by sequencing (see Example 2 Part B) and named pTrcHBS (FIG. 2).

TABLE 4

Primers used in cloning of heparin binding site
Primers for HBS cloning

| | |
|---|---|
| 5' → 3' | CGGGATCCGCAAGCAAAACATAAA-CAGCGCAAACGCGGTACC CC (SEQ ID NO: 19) |
| 3' → 5' | GGGGTACCGCGTTTCCGCTGTTTAT-GTTTTGCTTGCGGATCC CG (SEQ ID NO: 20) |

B. Amplification of the Mature Parts of BMP-3c/138 and BMP-3c/110 and Cloning into pGEM®-T Vector Kpn I restriction sites were created in front of the mature parts of rdBMPs with PCR method. Templates in these reactions were BMP genes cloned in pTrcHis2A vector between Bam HI and Hind III restriction sites (Example 2 Part D). Primers (Sigma-Genosys) designed for these reactions are in table 5.

TABLE 5

Primers used in PCR reaction creating kpn I and Hind III restriction sites in BMPs

| Gene | Primer |
|---|---|
| BMP-3c/138 | 5' 5' GGTACCAGGAAGAAGGGCCAGGATGTTTTC 3' (SEQ ID NO: 21)<br>3' 5' AAGCTTTTGGCAGGCACAGGTCTCCACAG 3' (SEQ ID NO: 22) |
| BMP-3c/110 | 5' 5' GGTACCCAATGGGATGAGCCACGGGTC 3' (SEQ ID NO: 23)<br>3' 5' AAGCTTTTGGCAGGCACAGGTCTCCACAG 3' (SEQ ID NO: 24) |

PCR reactions were done with Expand High Fidelity System (Roche). Reactions contained: HF buffer, 1.5 mM $MgCl_2$, 200 µM dNTP mix, 0.8 µM both oligos, 15 ng template DNA and 3.5 U High Fidelity Enzyme mix. Program used in reactions was: 94° C. 4 min, 25 cycles; 94° C. 1 min, 55° C. 1 min, 72° C. 2 min, one cycle; 72° C. 10 min and temperature was lowered to 4° C.

Sizes of the PCR products were examined with 1% agarose gels. Standard used in gels was either 500 µg of 100 bp Ladder (BioLabs) or 100 bp Ladder XIV (Roche). One fifth of the PCR reactions were loaded in agarose gels with Bromphenol Blue DNA loading buffer. Samples were run in 1×TAE buffer (40 mM Tris, 10 mM sodium acetate, 1 mM EDTA pH 7.8) with 70 V for 35 min and pictures of the gels were taken under UV-light.

PCR products were purified from 1% SeaPlague®GTG® low melting temperature agarose (BioProducts) with Wizard® PCR Preps DNA purification system (Promega) according to manufactures protocol.

Purified DNA fragments from PCR reactions were ligated in pGEM®-T vector with pGEM®-T and pGEM®-T Easy Vector System (Promega). Reactions contained; Rapid Ligation buffer, 50 ng pGEM®-T vector, 15-20 ng of insert DNA and 3 U T4 DNA Ligase. Ligations were performed in 16° C. water bath which was allowed to cool down to 4° C. slowly overnight.

Before transformation ligation-mixes were digested with 15 U Bam HI (Roche) in B-buffer (Roche) to remove possible traces from PCR reaction template (BMP in pTrcHis2A). Digestion reactions were incubated 1.5 h in 37° C.

C. Transformation of Plasmids into *E. Coli* TOP10 Cells

Plasmids were transformed into competent *Escherichia coli* TOP10 cells (Invitrogen). TOP10 cells were made competent with calcium chloride/magnesium chloride procedure (see Example 1 part E).

Transformation of plasmids was performed as follows: digested lig-mix was mixed in 100 µl of TCM and added to 200 µl of competent TOP10 cells. Cells were incubated first 30 min on ice and then 3 min at 43° C. 0.8 ml of LB-glucose medium was added to cells and mixed by inverting the tube. Cells were left to grow for 45 min at 37° C. and plated on LB-glucose+AMP+IPTG+X-GAL plates.

Colonies from transformations were inoculated in 5 ml of LB-glucose+100 µl/ml ampicillin medium and grown overnight at 37° C. with shaking. Plasmids were isolated from overnight cultures with Wizard® Plus Minipreps DNA purification system (Promega) according to manufactures procedure.

Plasmids were further purified with EtOH precipitation: 5 µl of 3 M sodium acetate pH 5.8 and 150 µl of absolute ethanol were added to purified plasmids in water and DNA was left to precipitate at −20° C. overnight. In the next morning reactions were centrifuged in microcentrifuge 14000 rpm at 4° C., supernatant was removed and precipitated DNA was washed with 500 µl of cold 70% EtOH. Samples were centrifuged again and washing step was repeated. DNA was air dried and resuspended in 20 µl of sterile water.

Nucleotide sequences of the inserts were checked with sequencing. Sequencing reactions contained 5 µM of both primers and 150-300 ng of plasmid DNA. Sequencing primers are shown in table 6.

TABLE 6

Sequencing primers for pGEM ®-T plasmids

| | | |
|---|---|---|
| 5' primer | TAATACGACTCACTATAGGGCGA | (SEQ ID NO: 25) |
| 3' primer | ATTTAGGTGACACTATAGAATAC | (SEQ ID NO: 26) |

B. Addition of the Mature Part of Reindeer BMP-3c/138 and BMP-3c/110 to pTrcHBS and Transformation the Competent *Escherichia coli* TOP10 F'

HBS sequence has previously been cloned into pTrcHis2A vector between Bam HI and Kpn I restriction sites (Example 4 part A). Before ligation, plasmid pTrcHBS as well as BMP-3c/138 and BMP-3c/110 in pGEM®-T were first digested with Kpn I and Hind III enzymes. BMP in pGEM®-T Kpn I digestion reactions contained 800 ng of plasmid DNA, 2×L buffer (Roche), 150 ng of BSA and 20 U of Kpn I (Roche). pTrcHBS Kpn I digestion reactions contained 250 ng of plasmid DNA, 2×L buffer (Roche), 150 ng of BSA and 20 U of Kpn I (Roche). Reactions were incubated at 37° C. for 3 h. B buffer (Roche) and 10 U of Hind III (Roche) were added to the reactions and reactions were further incubated at 37° C. for 1 h 30 min.

Ligation reactions contained Rapid Ligation buffer (Promega), 125 ng of double digested pTrcHBS vector, 400 ng of double digested BMP in pGEM®-T and 3 U of T4 DNA Ligase (Promega). Ligations were performed in 16° C. water bath which was allowed to cool down to 4° C. slowly overnight. Ligation mixes were digested in 1×H buffer (Roche) with 10 U of Pst I (Roche) and 12.5 U of EcoR I (Roche) to remove intact BMP in pGEM®-T and pTrc HBS plasmids. Reactions were incubated 1 h 30 min at 37° C.

BMP-3c/138 and BMP-3c/110 in pTrcHBS plasmids were transformed into competent *E. coli* TOP10 cells, amplified, purified and sequenced in the same way as described for pGEM®-T plasmids earlier. Sequencing primers for pTrcHis2A plasmids are shown in table 7. The new constructs were named pTrcHBSrd3c/138 and pTrcHBSrd3c/110 (FIG. 2) in TOP10 cells and were stored as glycerol stocks at −70° C. Glycerol stocks were made according to manufactures protocol (Invitrogen).

TABLE 7

Sequencing primers for pTrcHis2A plasmids

| | | |
|---|---|---|
| 5' primer | AGAGGTATATATTAATGTATCG | (SEQ ID NO: 27) |
| 3' primer | ATGGTCGACGGCGCTATTCAG | (SEQ ID NO: 28) |

C. Expression of the Recombinant Reindeer BMP-3c/138 and 3c/110 Mature Parts with Heparin Binding Site in *Escherichia coli* TOP10 Cell Cultures A pilot expression tests were done as follows; 2 ml of SOB medium containing 50 µg/ml ampicillin was inoculated with single recombinant TOP10 colony. Cells were grown overnight at 37° C. with shaking (225 rpm). In the morning 20 ml of fresh SOB medium with 50 µg/ml ampicillin was inoculated with 0.4 ml of overnight culture and cells were grown at 37° C. with shaking until $OD_{600}$ reached 0.6.

IPTG was added to a final concentration of 1 mM to induce the protein production in the cells. After induction cells were grown for 5 h at 37° C. with shaking. 0.5 ml samples were collected from culture at time points of 0 h, 1 h, 2 h, 3 h, 4 h, and 5 h after induction. Samples were centrifuged at 14000 rpm for 30 s and cell pellets were resuspended in 50 µl of Laemmli Sample buffer (BIO-RAD) containing 5% β-mercaptoethanol.

Samples resuspended in sample buffer were boiled for 5 min and spin down. 5 µl of each sample and 2 µl of Dual Color standard (BIO-RAD) was loaded in to 16.8% SDS-PAGE. Proteins with different sizes were separated in SDS buffer (25 mM Tris, 192 mM Glycine, 0.1% SDS) at 200 V for 1 h 10 min. SDS-gels were stained with Coomassie Brilliant Blue R-250 Staining Solution (BIO-RAD) and excess of the dye was removed with 1.7 M acetic acid—2.5 M methanol solution.

To express larger amounts of recombinant protein 50 ml of SOB medium containing 100 µg/ml ampicillin was inoculated with recombinant TOP10 colony. Cells were grown overnight at 37° C. with shaking (225 rpm). In the next morning 1200 ml of fresh SOB medium with 50 µg/ml ampicillin was inoculated with 25 ml of overnight culture. Recombinant cell cultures were grown at 37° C. with shaking until OD600 reached 0.6.

To induce the recombinant protein production in the cells IPTG was added to a final concentration of 1 mM. After induction cells were grown for 5 h at 37° C. with shaking. After incubation cultures were centrifuged at 5000 rpm for 17 min and cell pellets were collected and weighted.

Cells were pre-washed by suspending them first into $H_2O$ (g/5 ml) and centrifuged at 10000 rpm with SS-34 rotor for 20 min. Second washing step was done with the same ratio of 50 mM Na-phosphate buffer pH 7.0. Centrifugation was repeated and washing was continued with the same ratio of 25 mM Tris—10 mM EDTA pH 7.3 buffer. At the end of the pre-wash cells were centrifuged down once more and weighted.

Example 5

Isolation and Purification of Recombinant Reindeer BMP-3c/138 and BMP3c/110 Mature Part with Heparin Binding Site (HBSrdBMP-3c)

A. Collection of the *Escherichia Coli* TOP10 Cells and Isolation and Purification of Inclusion Bodies Cells were homogenized 1 g (wet weight) cells per 5 ml in cold 0.1 M Tris pH 7, 1 mM EDTA buffer. 1.5 mg Lysozyme (Roche) was added per g of cells in the mixture and cells were incubated 30 min at 4° C. Cells were disrupted with high-pressure homogenizator Cell Disruptor APV-2000. $MgCl_2$ was added to final concentration of 3 mM and DNase I (Roche) to final concentration of 10 μg/ml and mixture was incubated for 30 min at RT in order to digest DNA.

Half of the mixture volume of 60 mM EDTA, 6% Triton X-100, 1.5 M NaCl pH 7 puffer was added to the solution and mixture was incubated for 30 min at 4° C. Inclusion bodies were spin down by centrifugation at 12000 rpm for 10 min at 4° C. with SS-34 rotor. Pellet was resuspended in ratio of 8 ml per g of cells in 0.1 M Tris pH 7—20 mM EDTA buffer and centrifugation step was repeated. Inclusion body isolate was weighted and stored in −20° C.

B. IMAC Purification for HBSrdBMP-3c

Inclusion body isolate was mixed overnight with stirring to 35 mg/ml to 6 M GuHCl, 0.02 M $Na_2HPO_4$, 0.5 M NaCl pH 8 (lysis buffer). In the next morning solution was centrifuged at 12000 rpm for 20 min with SS-34 rotor. Supernatant was filtered trough Whatman GB 002 paper (Schleicher & Schuell). Centrifugation and filtration was repeated once and sample was stored at 4° C.

Pre-packed HiTrap Chelating HP affinity column (Amersham Biosciences) was charged with $Co^{2+}$ ions and equilibrated with sample buffer (lysis buffer pH 8) according to manufactures procedure. 30-40 ml of the filtrated protein sample was applied to the column and washed with 50 ml of lysis buffer pH 8. Second wash was done with 50 ml of 6 M urea, 0.02 M $Na_2HPO_4$, 0.5 M NaCl pH 8.

Desired protein with His6-tag was eluted out of the column with 200 ml of 6 M urea, 0.02 M $Na_2HPO_4$, 0.5 M NaCl pH 4. In final step column was washed with 200 ml of 6 M urea, 0.02 M $Na_2HPO_4$, 0.5 M NaCl, 0.5 M imidazole pH 8. 50 ml fractions were collected during every step. Samples from the fraction were analyzed with SDS-PAGE and fractions containing most recombinant protein were combined.

Example 6

Purification and Refolding of Recombinant Reindeer BMP-3c/138 and BMP3c/110 Mature Part with Heparin Binding Site (HBSrdBMP-3c)

A. IMAC Purification for HBSrdBMP-3c

*Escherichia coli* cells were lysed by shaking in 6 M GuHCl—20 mM Na-phosphate—0.5 M NaCl (pH 8.0) for 2 hours and filtrated through 45 μm filter. In IMAC purification method, pre-packed HiTrap Chelating HP affinity columns (Amersham Pharmacia Biotech) were used. Columns were charged with $Co^{2+}$, $Cu^{2+}$ or $Ni^{2+}$ ions according to instruction manual applied by supplier. Filtrated lysate was applied to the column and washed with 15 times the bed volume of lysis buffer. Second washing step was performed by 40 times the bed volume of 6 M urea—20 mM Na-phosphate—0.5 M NaCl (pH 7.5). In third washing buffer there was 0.05 M imidazole added into second washing buffer and the washing volume was 15 times the bed volume. Recombinant HBSrdBMP-3c was eluted from the column by imidazole gradient from 0.05 M to 0.5 M in 6 M urea—20 mM Na-phosphate—0.5 M NaCl (pH 7.5). The fractions were analyzed by SDS-PAGE and the ones containing the most highly purified recombinant HBSrdBMP-6 were combined and dialyzed against 100 mM Na-phosphate buffer (pH 7.5) over the weekend. Precipitated recombinant protein was collected by centrifugation and solved in 8 M urea—100 mM Na-phosphate—10 mM Tris-HCl (pH 7.5). Before heparin affinity column purification the recombinant protein solution was filtrated through 45 μm filter.

B. Heparin Affinity Column Purification for Recombinant HBSrdBMP-3c

Filtrate obtained after IMAC purification was applied in ready-to-use HiTrap Heparin HP column (Amersham Pharmacia Biotech) which was balanced with 8 M urea—100 mM Na-phosphate—10 mM Tris-HCl (pH 7.5). The column was then washed with 20 times bed volume of the same buffer and recombinant HBSrdBMP-3c was eluted from the heparin column by NaCl gradient from 0 M to 2 M also in the same buffer. The fractions analyzed by SDS-PAGE and Western blot analysis with the highest purity of HBSrdBMP-3c were combined. In Western blot analysis specific antibodies against His6 and BMP-3c were used. Combined fractions were ready for refolding procedure.

C. Refolding of Recombinant HBSrdBMP-3c/138 and HBSrdBMP-3c/110

Refolding of recombinant HBSrdBMP-3c was performed as described in Example 3 part D for recombinant rdBMP-3c.

Example 7

The Biological Activity Test of Recombinant Reindeer BMP-3c/138 and BMP-3c/110 Mature Part with and without Heparin Binding Site The biological activity of the lyophilized recombinant reindeer BMP-3c/138, BMP-3c/110, HBSrdBMP-3c/138 and HBSrdBMP-3c/110 was tested by implanting 1 mg, 3 mg and 5 mg of recombinant protein absorbed into Lyostrypt® collagen sponge or gelatin capsule in mouse tight muscle pouches. BSA was used as control. The hind legs were roentgenographed and the implant sites dissected and fixed in 10% neutral formalin solution. Fixed implants were cut into 7 μm sections and stained with hematoxylin-eosin staining. Sections were examined with a light microscope. The new bone formation as an area and optical density was evaluated by radiographs. The radiographic images were transferred into a computer by using an optical scanner (HP Scan Jet, Hewlett Packard, USA). Ectopic and orthopic new bone formations were evaluated as the areas ($mm^2$) of calcified tissue visible in the radiographs defined by using the Scion Image Beta 4.02 (Scion Corp., USA) software. The mean optical density (mmAl) of the defined area was measured with the same equipment. Calibration of the optical density was performed by using an aluminum wedge (Al) with 0.25 mmAl steps, giving a calibrated density range up to 4 mmAl.

Results

Cloning of Partial cDNA of Reindeer BMP-3c

The nucleotide sequence obtained from ABI Prism reactions was analyzed with computer and it was compared to already known BMP sequences. Due to homology searches the newly cloned cDNA seemed to be most homological with reindeer BMP-3b (nucleotide homology 96% and amino acid homology 95%) and with human BMP-3b (amino acid homology 93%), Table 1. The homologies of BMP-3c protein with the other mammalian BMP-3 proteins was highest by human BMP-3 (amino acid homology 91%), Table 2.

Expression of Reindeer BMP-3c Mature Part

First, two different parts of mature reindeer BMP-3c were inserted into pTrcHis2A vector and E. coli TOP 10 cells were transformed by resulted pTrcrd3c/138 and pTrcrd3c/110 vectors. Expression of recombinant protein was induced by IPTG. Recombinant protein production was checked by SDS-PAGE, but no induction was observed with both vectors. This was expected to be caused by several codons in rdBMP-3c which were rare for E. coli codon usage. It could be also possibly, that it is caused by slightly high GC content in the beginning of both rdBMP-3c protein coding sequence (by BMP-3c/138 the first 10 codons have a GC content of 53% and by BMP-3c/110 63%).

Figure 8:
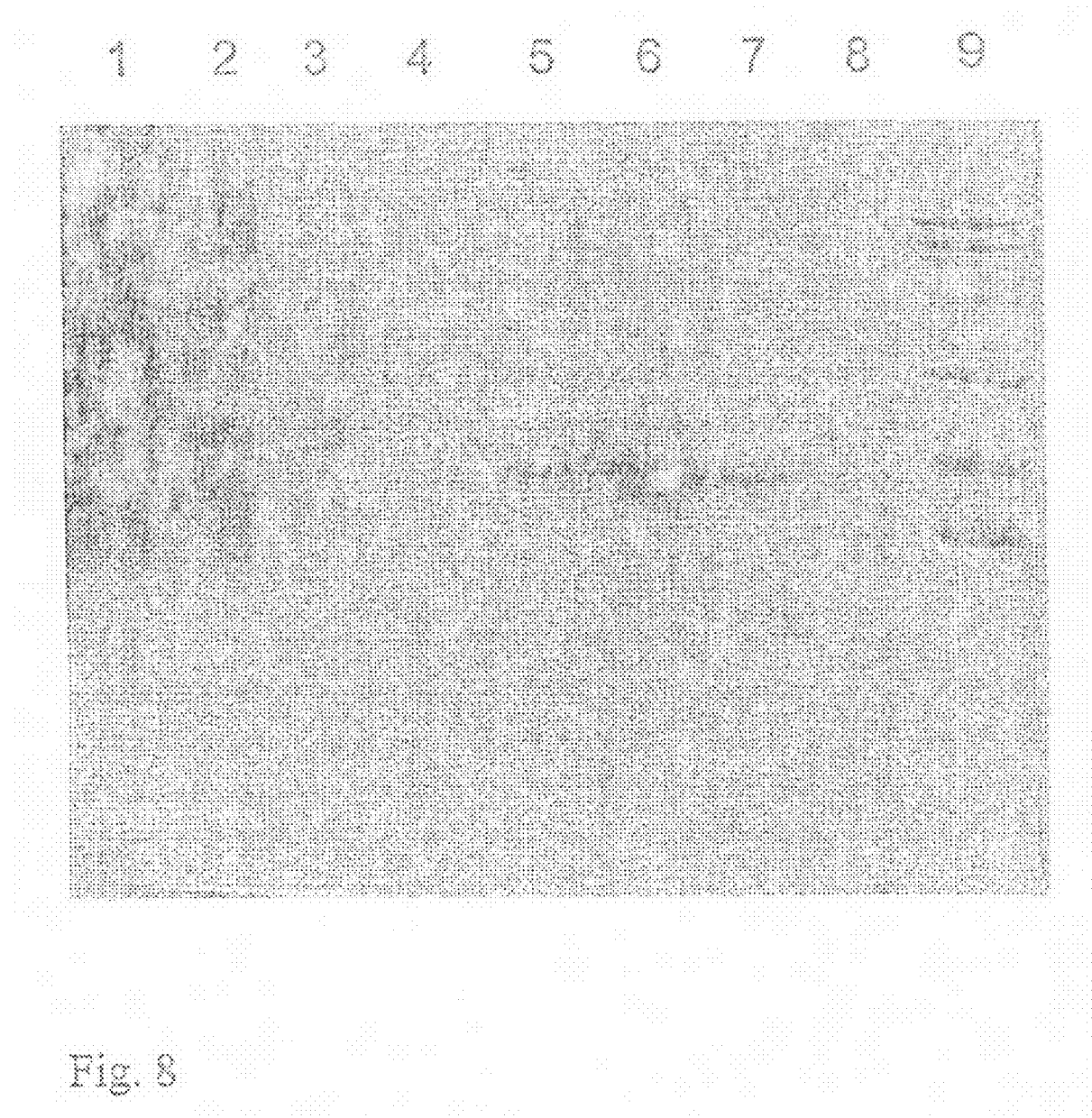
FIG. 8 shows a Coomassie stained SDS-PAGE of fractions eluted from HiTrap column (Example 3C). The bands represent 1) starting material, 2) flow through, 3) first wash, 4) second wash, 5) pH gradient elution pH 8, 6) pH-gradient elution pH 6.2, 7) pH-gradient elution pH 5.3 and 8) pH-gradient elution pH 4.0, 9) standard.

Because of these facts it was decided to try another vector system with different E. coli cell lines. pET22b(+) (Novagen) with His6-tag and pelB leader were chosen as the new expression vector and Rosetta (DE3) and Origami B (DE3) E. coli lines were chosen for expression. The DNA of both parts of the mature reindeer BMP-3c coding proteins were cloned into pET22b(+) and new plasmids were named as pETrd3c/138 and pETrd3c/110 and both Rosetta (DE3) and Origami B (DE3) cells were transformed with these constructed vectors. When analyzed in SDS-PAGE, overexpression of rdBMP-3c proteins was observed (FIG. 8). Due to expression studies mainly Rosetta (DE3) cells with pETrd3c vectors were used in producing recombinant rdBMP-3c proteins.

Purification of rdBMP-3c Proteins

Recombinant reindeer rdBMP-3c proteins were overexpressed in E. coli. After the wash treatment, isoelectric point precipitation and solubilization of the inclusion bodies the content of recombinant reindeer rdBMP-3c was 85%.

The next purification step was the immobilized metal affinity chromatography (IMAC). After the elution of the column with pH gradient, the purity of rdBMP-3c measured from the SDS-PAGE was up to 75% (FIG. 8). The isolated protein with the mature part of rdBMP-3c/138 had a MW of 20,400 Da and with the mature part of rdBMP-3c/110, 17,100 Da as shown by the electrophoretic mobility on SDS-PAGE under reducing conditions.

Purification of HBSrdBMP-3c Proteins

Recombinant reindeer HBSrdBMP-3c/138 and HBSrdBMP-3c/110 proteins were overexpressed in E. coli and produced as inclusion bodies (IBs). After the wash treatment, isoelectric point precipitation and solubilization of the inclusion bodies the content of recombinant reindeer HBSrdBMP-3c was 50%.

The next purification step was the affinity chromatography (IMAC and Heparin). After the elution of the columns, the purity of HBSrdBMP-3c measured from the SDS-PAGE was up to 90%. The isolated proteins with the mature part of HBSrdBMP-3c/138 had a MW of 20,300 Da and HBSrdBMP-3c/110 17,000 Da as shown by the electrophoretic mobility on SDS-PAGE under reducing conditions.

Refolding and Activity Tests of rdBMP-3c/138, rdBMP-3c/110, HBSrd3c/138 and HBSrd3c/110

The in vitro refolding of the denatured rdBMP-3c proteins was quantified by measuring of the refold dimer of the protein on Coomassie Brilliant Blue stained gels densitometrically. The amount of refolding measured by non-reducing SDS-PAGE was by the rdBMP-3c proteins without HBS 50% and by the HBSrdBMP-3c over 70%.

The osteoinductive activity induced by rdBMP-3c proteins without HBS was increased in dose dependent manner at least until 5 mg (Table 3). When compared the biological activity of BMP-3c/138 to BMP-3c/110 it seemed, that BMP-3c/110 was more potent inducer of bone formation. The fact, that refolding was 20% higher by the rdBMP-3c with HBS than without HBS, makes the HBSrdBMP-3c of great value.

This invention has been described with an emphasis upon some of the preferred embodiments and applications. However, it will be apparent for those skilled in the art that variations in the disclosed embodiments can be prepared and used and that the invention can be practiced otherwise than as specifically described herein within the scope of the following claims.

The invention claimed is:

1. An isolated bone morphogenetic protein (BMP-3), comprising the consensus amino acid sequence: R-K-K-Q-W-D-E-P-R-V/N-C-S/A-R-R-Y-L-K-V-D-F-A-D-I-G-W-N/S-E-W-I-I-S-P-K-S-F-D-A-Y-Y-C-S-G-A-C-E/Q-F-P-M-P-K-M-V/L-R/K-P-S-N-H-A-T-I-Q-S-I-V-R-A-V-G-I/V-V-P/S-G-I-P-E-P-C-C-V (SEQ ID NO: 29), and comprising an amino acid sequence having at least 80% identity with the amino acid sequence of SEQ ID NO: 1, said bone morphogenetic protein having osteogenic activity.

2. The bone morphogenetic protein of claim 1, comprising amino acids 26-104 of SEQ ID NO: 1.

3. The bone morphogenetic protein of claim 1, comprising amino acids 6-104 of SEQ ID NO: 1.

4. The bone morphogenetic protein of claim 1, comprising amino acids 6-109 of SEQ ID NO: 1.

5. The bone morphogenetic protein of claim 1, comprising the amino acid sequence of SEQ ID NO: 1.

6. The bone morphogenetic protein of claim 1, wherein the amino terminus of the protein comprises a heparin binding site having the amino acid sequence AKHKQRKRGT (SEQ ID NO: 7).

7. An isolated DNA molecule encoding the bone morphogenetic protein of claim 1.

8. A nucleotide vector comprising the DNA molecule of claim 7.

9. A recombinant host cell comprising the nucleotide vector of claim 8.

10. A pharmaceutical composition comprising the bone morphogenetic protein of claim 1.

11. The pharmaceutical composition of claim 10, comprising said bone morphogenetic protein as homodimer or as heterodimer together with another bone morphogenetic protein.

12. The pharmaceutical composition of claim 10, further comprising at least one of another bone morphogenetic protein, epidermal growth factor, fibroblast growth factor or transforming growth factor.

13. An osteogenic device comprising the bone morphogenetic protein of claim 1.

14. The osteogenic device of claim 13, comprising said bone morphogenetic protein as homodimer or as heterodimer together with another bone morphogenetic protein.

15. The osteogenic device of claim 13, further comprising at least one of another bone morphogenetic protein, epidermal growth factor, fibroblast growth factor or transforming growth factor.

16. The osteogenic device of claim 13, comprising a biocompatible matrix.

17. The osteogenic device of claim 16, wherein said biocompatible matrix comprises calcium phosphate, carboxy methyl cellulose, collagen or combinations thereof.

18. A method for inducing the formation of bone, cartilage, tendon or tooth in vitro or in vivo comprising treating said bone, cartilage, tendon or tooth with the bone morphogenetic protein of claim 1.

19. A method for treating disorders related to bone, cartilage, tendon or tooth wherein regeneration, repair or growth thereof is desired comprising administering the bone morphogenetic protein of claim 1 to a patient suffering from said disorder.

20. The pharmaceutical composition of claim 11, further comprising at least one of another bone morphogenetic protein, epidermal growth factor, fibroblast growth factor or transforming growth factor.

* * * * *

SEQUENCE LISTING

```
<160> NUMBER OF SEQ ID NOS: 35

<210> SEQ ID NO 1
<211> LENGTH: 138
<212> TYPE: PRT
<213> ORGANISM: Rangifer tarandus

<400> SEQUENCE: 1

Arg Lys Lys Gly Gln Asp Val Phe Met Ala Ser Ser Gln Val Leu Asp
1               5                   10                  15

Phe Asp Glu Lys Thr Met Gln Lys Ala Arg Lys Lys Gln Trp Asp Glu
            20                  25                  30

Pro Arg Val Cys Ser Arg Arg Tyr Leu Lys Val Asp Phe Ala Asp Ile
        35                  40                  45

Gly Trp Asn Glu Trp Ile Ile Ser Pro Lys Ser Phe Asp Ala Tyr Tyr
    50                  55                  60

Cys Ser Gly Ala Cys Glu Phe Pro Met Pro Lys Met Val Arg Pro Ser
65                  70                  75                  80

Asn His Ala Thr Ile Gln Ser Ile Val Arg Ala Val Gly Ile Val Pro
```

```
                85                  90                  95
Gly Ile Pro Glu Pro Cys Cys Val Pro Asp Lys Met Ser Ser Leu Gly
            100                 105                 110

Val Leu Phe Leu Asp Glu Asn Arg Asn Val Val Leu Lys Val Tyr Pro
        115                 120                 125

Asn Met Ser Val Glu Thr Cys Ala Cys Gln
    130                 135

<210> SEQ ID NO 2
<211> LENGTH: 137
<212> TYPE: PRT
<213> ORGANISM: Rangifer tarandus

<400> SEQUENCE: 2

Arg Lys Lys Gly Gln Asp Val Phe Met Ala Ser Ser Gln Val Leu Asp
1               5                   10                  15

Phe Asp Glu Lys Thr Met Gln Lys Ala Lys Lys Gln Val Gly Glu Pro
            20                  25                  30

Arg Val Cys Ser Arg Arg Tyr Leu Lys Val Asp Phe Ala Asp Ile Gly
        35                  40                  45

Trp Asn Glu Trp Ile Ile Ser Pro Lys Ser Phe Asp Ala Tyr Tyr Cys
    50                  55                  60

Ser Gly Ala Cys Glu Phe Pro Met Pro Arg Trp Val Arg Pro Ser Asn
65                  70                  75                  80

His Ala Thr Ile Gln Ser Ile Val Arg Ala Val Gly Ile Val Pro Gly
                85                  90                  95

Ile Pro Glu Pro Cys Cys Ala Pro Asp Lys Met Ser Ser Leu Gly Val
            100                 105                 110

Leu Phe Leu Asp Glu Asn Arg Asn Val Val Leu Lys Val Tyr Pro Asn
        115                 120                 125

Met Ser Val Glu Thr Cys Ala Cys Gln
    130                 135

<210> SEQ ID NO 3
<211> LENGTH: 138
<212> TYPE: PRT
<213> ORGANISM: Homo sapiens

<400> SEQUENCE: 3

Arg Lys Lys Gly Gln Glu Val Phe Met Ala Ala Ser Gln Val Leu Asp
1               5                   10                  15

Phe Asp Glu Lys Thr Met Gln Lys Ala Arg Arg Lys Gln Trp Asp Glu
            20                  25                  30

Pro Arg Val Cys Ser Arg Arg Tyr Leu Lys Val Asp Phe Ala Asp Ile
        35                  40                  45

Gly Trp Asn Glu Trp Ile Ile Ser Pro Lys Ser Phe Asp Ala Tyr Tyr
    50                  55                  60

Cys Ala Gly Ala Cys Glu Phe Pro Met Pro Lys Ile Val Arg Pro Ser
65                  70                  75                  80

Asn His Ala Thr Ile Gln Ser Ile Val Arg Ala Val Gly Ile Ile Pro
                85                  90                  95

Gly Ile Pro Glu Pro Cys Cys Val Pro Asp Lys Met Asn Ser Leu Gly
            100                 105                 110

Val Leu Phe Leu Asp Glu Asn Arg Asn Val Val Leu Lys Val Tyr Pro
        115                 120                 125

Asn Met Ser Val Asp Thr Cys Ala Cys Arg
```

<210> SEQ ID NO 4
<211> LENGTH: 138
<212> TYPE: PRT
<213> ORGANISM: Homo sapiens

<400> SEQUENCE: 4

```
Lys Lys Lys Gln Arg Lys Gly Pro His Arg Lys Ser Gln Thr Leu Gln
1               5                   10                  15

Phe Asp Glu Gln Thr Leu Lys Lys Ala Arg Arg Lys Gln Trp Ile Glu
                20                  25                  30

Pro Arg Asn Cys Ala Arg Arg Tyr Leu Lys Val Asp Phe Ala Asp Ile
            35                  40                  45

Gly Trp Ser Glu Trp Ile Ile Ser Pro Lys Ser Phe Asp Ala Tyr Tyr
        50                  55                  60

Cys Ser Gly Ala Cys Gln Phe Pro Met Pro Lys Ser Leu Lys Pro Ser
65                  70                  75                  80

Asn His Ala Thr Ile Gln Ser Ile Val Arg Ala Val Gly Val Val Pro
                85                  90                  95

Gly Ile Pro Glu Pro Cys Cys Val Pro Glu Lys Met Ser Ser Leu Ser
            100                 105                 110

Ile Leu Phe Phe Asp Glu Asn Lys Asn Val Val Leu Lys Val Tyr Pro
        115                 120                 125

Asn Met Thr Val Glu Ser Cys Ala Cys Arg
    130                 135
```

<210> SEQ ID NO 5
<211> LENGTH: 138
<212> TYPE: PRT
<213> ORGANISM: Rattus norvegicus

<400> SEQUENCE: 5

```
Lys Lys Lys Gln Arg Lys Gly Pro His Gln Lys Gly Gln Thr Leu Gln
1               5                   10                  15

Phe Asp Glu Gln Thr Leu Lys Lys Ala Arg Arg Lys Gln Trp Ile Glu
                20                  25                  30

Pro Arg Asn Cys Ala Arg Arg Tyr Leu Lys Val Asp Phe Ala Asp Ile
            35                  40                  45

Gly Trp Ser Glu Trp Ile Ile Ser Pro Lys Ser Phe Asp Ala Tyr Tyr
        50                  55                  60

Cys Ser Gly Ala Cys Gln Phe Pro Met Pro Lys Ser Leu Lys Pro Ser
65                  70                  75                  80

Asn His Ala Thr Ile Gln Ser Ile Val Arg Ala Val Gly Val Val Ser
                85                  90                  95

Gly Ile Pro Glu Pro Cys Cys Val Pro Glu Lys Met Ser Ser Leu Ser
            100                 105                 110

Ile Leu Phe Phe Asp Glu Asn Lys Asn Val Val Leu Lys Val Tyr Pro
        115                 120                 125

Asn Met Thr Val Asp Ser Cys Ala Cys Arg
    130                 135
```

<210> SEQ ID NO 6
<211> LENGTH: 138
<212> TYPE: PRT
<213> ORGANISM: Xenopus laevis

<400> SEQUENCE: 6

```
Lys Lys Lys Leu Arg Lys Gly Ser Arg Gln Lys Ser Gln Thr Leu Gln
1               5                   10                  15

Phe Asp Glu Gln Thr Leu Lys Lys Ala Arg Arg Lys Gln Trp Asn Glu
            20                  25                  30

Pro Arg Asn Cys Ala Arg Arg Tyr Leu Lys Val Asp Phe Ala Asp Ile
            35                  40                  45

Gly Trp Ser Glu Trp Ile Ile Ser Pro Lys Ser Phe Asp Ala Tyr Tyr
        50                  55                  60

Cys Ser Gly Ala Cys Gln Phe Pro Met Pro Lys Ser Leu Lys Pro Ser
65              70                  75                  80

Asn His Ala Thr Ile Gln Ser Ile Val Arg Ala Val Gly Val Val Pro
                85                  90                  95

Gly Ile Pro Glu Pro Cys Cys Val Pro Glu Lys Met Ser Ser Leu Ser
            100                 105                 110

Ile Leu Phe Leu Asp Glu Asn Lys Asn Val Val Leu Lys Val Tyr Pro
            115                 120                 125

Asn Met Thr Val Glu Ser Cys Ala Cys Arg
            130                 135

<210> SEQ ID NO 7
<211> LENGTH: 10
<212> TYPE: PRT
<213> ORGANISM: Rangifer tarandus

<400> SEQUENCE: 7

Ala Lys His Lys Gln Arg Lys Arg Gly Thr
1               5                   10

<210> SEQ ID NO 8
<211> LENGTH: 11
<212> TYPE: PRT
<213> ORGANISM: Rangifer tarandus

<400> SEQUENCE: 8

Gln Ala Lys His Lys Gln Arg Lys Arg Gly Thr
1               5                   10

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9
cgcaargacc gcargaagaa rggc                                          24

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
tcygtrgaga cctgtgcctg ycaa                                          24

<210> SEQ ID NO 11
<211> LENGTH: 23
```

<212> TYPE: DNA
<213> ORGANISM: Artificial Sequence
<220> FEATURE:
<223> OTHER INFORMATION: Description of Artificial Sequence: Synthetic Primer

<400> SEQUENCE: 11
taatacgact cactataggg cga                                           23

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic Primer

<400> SEQUENCE: 12
atttaggtga cactatagaa tac                                           23

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence: Synthetic Primer

<400> SEQUENCE: 13
ggatccgagg aagaagggcc aggatgttttt c                                 31

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Synthetic Primer

<400> SEQUENCE: 14
aagcttttgg caggcacagg tctccac                                       27

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic Primer

<400> SEQUENCE: 15
agaggtatat attaatgtat cg                                            22

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic Primer

<400> SEQUENCE: 16
atggtcgacg gcgctattca g                                             21

<210> SEQ ID NO 17
<211> LENGTH: 31
<212> TYPE: DNA

<213> ORGANISM: Artificial Sequence
<220> FEATURE:
<223> OTHER INFORMATION: Description of Artificial Sequence: Synthetic
      Primer

<400> SEQUENCE: 17
ggatccgagg aagaagggcc aggatgtttt c                              31

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 18
cgcaagcttt tggcaggcac aggtctccac                                30

<210> SEQ ID NO 19
<211> LENGTH: 44
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 19
cgggatccgc aagcaaaaca taaacagcgc aaacgcggta cccc                44

<210> SEQ ID NO 20
<211> LENGTH: 44
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 20
ggggtaccgc gtttccgctg tttatgtttt gcttgcggat cccg                44

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 21
ggtaccagga agaagggcca ggatgttttc                                30

<210> SEQ ID NO 22
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 22
aagcttttgg caggcacagg tctccacag                                 29

<210> SEQ ID NO 23
<211> LENGTH: 27
<212> TYPE: DNA
<213> ORGANISM: Artificial Sequence -continued
<220> FEATURE:
<223> OTHER INFORMATION: Description of Artificial Sequence: Synthetic
      Primer

<400> SEQUENCE: 23
ggtacccaat gggatgagcc acgggtc                                              27

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 24
aagcttttgg caggcacagg tctccacag                                            29

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 25
taatacgact cactataggg cga                                                  23

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 26
atttaggtga cactatagaa tac                                                  23

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 27
agaggtatat attaatgtat cg                                                   22

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 28
atggtcgacg gcgctattca g                                                    21

<210> SEQ ID NO 29
<211> LENGTH: 79
<212> TYPE: PRT
<213> ORGANISM: Artificial Sequence
<220> FEATURE:

```
<223> OTHER INFORMATION: Description of Artificial Sequence: Synthetic
      Peptide
<220> FEATURE:
<221> NAME/KEY: MISC_FEATURE
<222> LOCATION: (10)..(10)
<223> OTHER INFORMATION: Xaa = Val or Asn
<220> FEATURE:
<221> NAME/KEY: MISC_FEATURE
<222> LOCATION: (12)..(12)
<223> OTHER INFORMATION: Xaa = Ser or Ala
<220> FEATURE:
<221> NAME/KEY: MISC_FEATURE
<222> LOCATION: (26)..(26)
<223> OTHER INFORMATION: Xaa = Asn or Ser
<220> FEATURE:
<221> NAME/KEY: MISC_FEATURE
<222> LOCATION: (45)..(45)
<223> OTHER INFORMATION: Xaa = Glu or Gln
<220> FEATURE:
<221> NAME/KEY: MISC_FEATURE
<222> LOCATION: (52)..(52)
<223> OTHER INFORMATION: Xaa = Val or Leu
<220> FEATURE:
<221> NAME/KEY: MISC_FEATURE
<222> LOCATION: (53)..(53)
<223> OTHER INFORMATION: Xaa = Arg or Lys
<220> FEATURE:
<221> NAME/KEY: MISC_FEATURE
<222> LOCATION: (69)..(69)
<223> OTHER INFORMATION: Xaa = Ile or Val
<220> FEATURE:
<221> NAME/KEY: MISC_FEATURE
<222> LOCATION: (71)..(71)
<223> OTHER INFORMATION: Xaa = Pro or Ser

<400> SEQUENCE: 29

Arg Lys Lys Gln Trp Asp Glu Pro Arg Xaa Cys Xaa Arg Arg Tyr Leu
1               5                   10                  15

Lys Val Asp Phe Ala Asp Ile Gly Trp Xaa Glu Trp Ile Ile Ser Pro
            20                  25                  30

Lys Ser Phe Asp Ala Tyr Tyr Cys Ser Gly Ala Cys Xaa Phe Pro Met
        35                  40                  45

Pro Lys Met Xaa Xaa Pro Ser Asn His Ala Thr Ile Gln Ser Ile Val
    50                  55                  60

Arg Ala Val Gly Xaa Val Xaa Gly Ile Pro Glu Pro Cys Cys Val
65                  70                  75

<210> SEQ ID NO 30
<211> LENGTH: 501
<212> TYPE: DNA
<213> ORGANISM: Rangifer tarandus

<400> SEQUENCE: 30
atggatccga ggaagaaggg ccaggatgtt tcatggcct cctcacaggt gctggacttt      60
gacgagaaga cgatgcagaa agcccggaag aagcaatggg atgagccacg ggtctgttcc    120
cggaggtatc tgaaggtgga cttcgcggcc atagggtgga tgaatggat catctcaccc     180 aagtctttcg acgcctacta ctgctcagga gcctgcgagt tccccatgcc aagatggtc    240 cgcccatcca accacgccac catccagagc atcgtcaggg ccgtgggcat cgtcccaggc    300
atcccagagc cgtgctgtgt tcccgacaag atgagctctc ttggggtcct tttcctggat   360
gagaaccgga acgtgctact gaaggtgtac cccaacatgt ctgtggagac ctgtgcctgc   420
caaaagcttg ggcccgaaca aaaactcatc tcagaagagg atctgaatag cgccgtcgac   480
catcatcatc atcatcattg a                                             501
```

<210> SEQ ID NO 31
<211> LENGTH: 166
<212> TYPE: PRT
<213> ORGANISM: Rangifer tarandus

<400> SEQUENCE: 31

```
Met Asp Pro Arg Lys Gly Gln Asp Val Phe Met Ala Ser Ser Gln
1               5                   10                  15

Val Leu Asp Phe Asp Glu Lys Thr Met Gln Lys Ala Arg Lys Lys Gln
            20                  25                  30

Trp Asp Glu Pro Arg Val Cys Ser Arg Arg Tyr Leu Lys Val Asp Phe
        35                  40                  45

Ala Asp Ile Gly Trp Asn Glu Trp Ile Ile Ser Pro Lys Ser Phe Asp
    50                  55                  60

Ala Tyr Tyr Cys Ser Gly Ala Cys Glu Phe Pro Met Pro Lys Met Val
65                  70                  75                  80

Arg Pro Ser Asn His Ala Thr Ile Gln Ser Ile Val Arg Ala Val Gly
                85                  90                  95

Ile Val Pro Gly Ile Pro Glu Pro Cys Cys Val Pro Asp Lys Met Ser
            100                 105                 110

Ser Leu Gly Val Leu Phe Leu Asp Glu Asn Arg Asn Val Val Leu Lys
        115                 120                 125

Val Tyr Pro Asn Met Ser Val Glu Thr Cys Ala Cys Gln Lys Leu Gly
    130                 135                 140

Pro Glu Gln Lys Leu Ile Ser Glu Glu Asp Leu Asn Ser Ala Val Asp
145                 150                 155                 160

His His His His His His
                165
```

<210> SEQ ID NO 32
<211> LENGTH: 549
<212> TYPE: DNA
<213> ORGANISM: Rangifer tarandus

<400> SEQUENCE: 32

```
atgaaatacc tgctgccgac cgctgctgct ggtctgctgc tcctcgctgc ccagccggcg      60
atggccatgg atatcggaat taattcggat ccgaggaaga agggccagga tgttttcatg     120
gcctcctcac aggtgctgga ctttgacgag aagacgatgc agaaagcccg gaagaagcaa     180
tgggatgagc cacgggtctg ttcccggagg tatctgaagg tggacttcgc ggacataggg     240
tggaatgaat ggatcatctc acccaagtct ttcgacgcct actactgctc aggagcctgc     300
gagttcccca tgcccaagat ggtccgccca tccaaccacg ccaccatcca gagcatcgtc     360
agggccgtgg gcatcgtccc aggcatccca gagccgtgct gtgttcccga caagatgagc     420
tctcttgggg tcctttttcct ggatgagaac cggaacgtgg tactgaaggt gtaccccaac    480
atgtctgtgg agacctgtgc ctgccaaaag cttgcggccg caatagagca ccaccaccac     540
caccactga                                                             549
```

<210> SEQ ID NO 33
<211> LENGTH: 182
<212> TYPE: PRT
<213> ORGANISM: Rangifer tarandus

<400> SEQUENCE: 33

```
Met Lys Tyr Leu Leu Pro Thr Ala Ala Ala Gly Leu Leu Leu Leu Ala
1               5                   10                  15
```

Ala Gln Pro Ala Met Ala Met Pro Ile Gly Ile Asn Ser Asp Pro Arg
            20                  25                  30

Lys Lys Gly Gln Asp Val Phe Met Ala Ser Ser Gln Val Leu Asp Phe
        35                  40                  45

Asp Glu Lys Thr Met Gln Lys Ala Arg Lys Lys Gln Trp Asp Glu Pro
    50                  55                  60

Arg Val Cys Ser Arg Arg Tyr Leu Lys Val Asp Phe Ala Asp Ile Gly
65                  70                  75                  80

Trp Asn Glu Trp Ile Ile Ser Pro Lys Ser Phe Asp Ala Tyr Tyr Cys
                85                  90                  95

Ser Gly Ala Cys Glu Phe Pro Met Pro Lys Met Val Arg Pro Ser Asn
            100                 105                 110

His Ala Thr Ile Gln Ser Ile Val Arg Ala Val Gly Ile Val Pro Gly
        115                 120                 125

Ile Pro Glu Pro Cys Cys Val Pro Asp Lys Met Ser Ser Leu Gly Val
    130                 135                 140

Leu Phe Leu Asp Glu Asn Arg Asn Val Val Leu Lys Val Tyr Pro Asn
145                 150                 155                 160

Met Ser Val Glu Thr Cys Ala Cys Gln Lys Leu Ala Ala Ala Leu Glu
                165                 170                 175

His His His His His His
            180

<210> SEQ ID NO 34
<211> LENGTH: 426
<212> TYPE: DNA
<213> ORGANISM: Rangifer tarandus

<400> SEQUENCE: 34
cgcaaggacc gccggaagaa gggccaggat gttttcatgg cctcctcaca ggtgctggac      60
tttgacgaga gacgatgca gaaagcccgg aagaagcaat gggatgagcc acgggtctgt     120
tcccggaggt atctgaaggt ggacttcgcg gacatagggt ggaatgaatg gatcatctca     180
cccaagtctt tcgacgccta ctactgctca ggagcctgcg agttccccat gcccaagatg     240
gtccgcccat ccaaccacgc caccatccag agcatcgtca gggccgtggg catcgtccca     300
ggcatcccag agccgtgctg tgttcccgac aagatgagct ctcttccggt ccttttcctg     360
gatgagaacc ggaacgtggt actgaaggtg taccccaca tgtctgtgga gacctgtgcc     420
tgccaa                                                                426

<210> SEQ ID NO 35
<211> LENGTH: 142
<212> TYPE: PRT
<213> ORGANISM: Rangifer tarandus

<400> SEQUENCE: 35

Arg Lys Asp Arg Arg Lys Lys Gly Gln Asp Val Phe Met Ala Ser Ser
1               5                   10                  15

Gln Val Leu Asp Phe Asp Glu Lys Thr Met Gln Lys Ala Arg Lys Lys
            20                  25                  30

Gln Trp Asp Glu Pro Arg Val Cys Ser Arg Arg Tyr Leu Lys Val Asp
        35                  40                  45

Phe Ala Asp Ile Gly Trp Asn Glu Trp Ile Ile Ser Pro Lys Ser Phe
    50                  55                  60

Asp Ala Tyr Tyr Cys Ser Gly Ala Cys Glu Phe Pro Met Pro Lys Met
65                  70                  75                  80

-continued

```
Val Arg Pro Ser Asn His Ala Thr Ile Gln Ser Ile Val Arg Ala Val
                 85              90              95

Gly Ile Val Pro Gly Ile Pro Glu Pro Cys Cys Val Pro Asp Lys Met
            100             105             110

Ser Ser Leu Gly Val Leu Phe Leu Asp Glu Asn Arg Asn Val Val Leu
        115             120             125

Lys Val Tyr Pro Asn Met Ser Val Glu Thr Cys Ala Cys Gln
    130             135             140
```